(12) United States Patent
Jiang et al.

(10) Patent No.: US 10,938,068 B2
(45) Date of Patent: Mar. 2, 2021

(54) LITHIUM-ION BATTERY AND APPARATUS

(71) Applicant: Contemporary Amperex Technology Co., Limited, Fujian (CN)

(72) Inventors: Yao Jiang, Fujian (CN); Chunhua Hu, Fujian (CN); Tiancheng Yi, Fujian (CN); Shushi Dou, Fujian (CN); Chengdu Liang, Ningde (CN)

(73) Assignee: Contemporary Amperex Technology Co., Limited, Ningde (CN)

( * ) Notice: Subject to any disclaimer, the term of this patent is extended or adjusted under 35 U.S.C. 154(b) by 0 days.

(21) Appl. No.: 17/043,683

(22) PCT Filed: Dec. 13, 2019

(86) PCT No.: PCT/CN2019/125323
§ 371 (c)(1),
(2) Date: Sep. 30, 2020

(87) PCT Pub. No.: WO2020/119805
PCT Pub. Date: Jun. 18, 2020

(65) Prior Publication Data
US 2021/0036368 A1 Feb. 4, 2021

(30) Foreign Application Priority Data
Dec. 14, 2018 (CN) .......................... 201811537017.5

(51) Int. Cl.
*H01M 10/05* (2010.01)
*H01M 4/52* (2010.01)
(Continued)

(52) U.S. Cl.
CPC ...... *H01M 10/0567* (2013.01); *C07D 239/04* (2013.01); *C07D 241/04* (2013.01);
(Continued)

(58) Field of Classification Search
None
See application file for complete search history.

(56) References Cited

U.S. PATENT DOCUMENTS

2017/0069934 A1  3/2017  Kim et al.

FOREIGN PATENT DOCUMENTS

CN   103022556 A   4/2013
CN   105655639 A   6/2016
(Continued)

OTHER PUBLICATIONS

PCT International Search Report for PCT/CN2019/125323, dated Jan. 23, 2020, 19 pages.

*Primary Examiner* — Jonathan Crepeau
*Assistant Examiner* — Angela J Martin
(74) *Attorney, Agent, or Firm* — Law Offices of Liaoteng Wang

(57) ABSTRACT

This application provides a lithium-ion battery and an apparatus. The lithium-ion battery includes an electrode assembly and an electrolyte. The electrode assembly includes a positive electrode plate, a negative electrode plate, and a separator. A positive active material of the positive electrode plate includes $Li_{x1}Co_{y1}M_{1-y1}O_{2-z1}Q_{z1}$, where $0.5 \leq x1 \leq 1.2$, $0.8 \leq y1 < 1.0$, $0 \leq z1 \leq 0.1$, M is selected from one or more of Al, Ti, Zr, Y, and Mg, and Q is selected from one or more of F, Cl, and S. The electrolyte contains an additive A, an additive B, and an additive C. The additive A is a polynitrile six-membered nitrogen-heterocyclic compound with a relatively low oxidation potential. The additive B is an anhydride compound. The additive C is a halogen substituted cyclic carbonate compound.

18 Claims, 4 Drawing Sheets

(51) Int. Cl.
*C07D 239/04* (2006.01)
*C07D 251/04* (2006.01)
*H01M 10/0567* (2010.01)
*H01M 10/0525* (2010.01)
*H01M 4/525* (2010.01)
*C07D 241/04* (2006.01)
*H01M 4/02* (2006.01)

(52) U.S. Cl.
CPC .......... *C07D 251/04* (2013.01); *H01M 4/525* (2013.01); *H01M 10/0525* (2013.01); *H01M 2004/028* (2013.01); *H01M 2300/0025* (2013.01)

(56) References Cited

FOREIGN PATENT DOCUMENTS

| | | |
|---|---|---|
| CN | 107431197 A | 12/2017 |
| CN | 109148950 A | 1/2019 |
| CN | 110391460 A | 10/2019 |
| JP | 2012104439 A | 5/2012 |

LITHIUM-ION BATTERY AND APPARATUS

CROSS-REFERENCE TO RELATED APPLICATION

This application is a National Stage of International Application No. PCT/CN2019/125323, filed on Dec. 13, 2019, which claims priority to Chinese Patent Application No. 201811537017.5, filed on Dec. 14, 2018, both of which are incorporated herein by reference in their entireties.

TECHNICAL FIELD

This application relates to the field of energy storage materials, and in particular, to a lithium-ion battery and an apparatus.

BACKGROUND

Lithium-ion batteries are widely applied to electromobiles and consumer electronic products due to their advantages such as high energy density, high output power, long cycle life, and low environmental pollution. Current requirements on lithium-ion batteries are high voltage, high power, long cycle life, long storage life, and superb safety performance.

Currently, $LiCoO_2$ is widely used as a positive active material in lithium-ion batteries, and shows relatively stable performance during cycling between fully discharged $LiCoO_2$ and semi-charged $Li_{0.5}CoO_2$ (4.2 V vs. Li). Therefore, lithium ions that are actually used account only for ½ of lithium ions actually contained in $LiCoO_2$. When the voltage is greater than 4.2 V, the remaining ½ of lithium ions contained in $LiCoO_2$ may continue to be extracted. However, during deep delithiation, $Co^{3+}$ is oxidized into quite unstable $Co^{4+}$, which oxidizes an electrolyte together with surface oxygen that loses a large quantity of electrons. In this case, a large amount of gas is produced inside the batteries, causing the batteries to swell. In addition, due to a corrosive effect of HF in the electrolyte on a surface of a positive electrode, $Co^{4+}$ is dissolved in the electrolyte and deposited on a surface of a negative electrode, catalyzing reduction of the electrolyte, and also producing a large amount of gas that causes the batteries to swell. In addition, due to high overlapping between a 3d energy level of Co and a 2p energy level of O, the deep delithiation also causes lattice oxygen to lose a large quantity of electrons, resulting in sharp shrinkage of $LiCoO_2$ unit cells along a c-axis direction, and leading to instability or even collapse of a local bulk structure. This eventually causes loss of $LiCoO_2$ active sites, and a rapid decrease in capacity of the lithium-ion batteries. Therefore, $LiCoO_2$ has very poor performance when being used in a high-voltage system greater than 4.2 V.

In view of this, this application is hereby proposed.

SUMMARY

In view of the problems in the background, an objective of this application is to provide a lithium-ion battery and an apparatus. The lithium-ion battery has superb cycle performance and storage performance, especially under high-temperature and high-voltage conditions.

To achieve the foregoing objective, according to a first aspect, this application provides a lithium-ion battery, including an electrode assembly and an electrolyte, wherein the electrode assembly includes a positive electrode plate, a negative electrode plate, and a separator. A positive active material of the positive electrode plate includes $Li_{x1}Co_{y1}M_{1-y1}O_{2-z1}Q_{z1}$, where $0.5 \leq x1 \leq 1.2$, $0.8 \leq y1 < 1.0$, $0 \leq z1 \leq 0.1$, M is selected from one or more of Al, Ti, Zr, Y, and Mg, and Q is selected from one or more of F, Cl, and S. The electrolyte contains an additive A, an additive B, and an additive C, and the additive A is selected from one or more of compounds represented by Formula I-1, Formula I-2, and Formula I-3; the additive B is selected from one or more of compounds represented by Formula II-1 and Formula II-2; and the additive C is selected from one or more of compounds represented by Formula III-1.

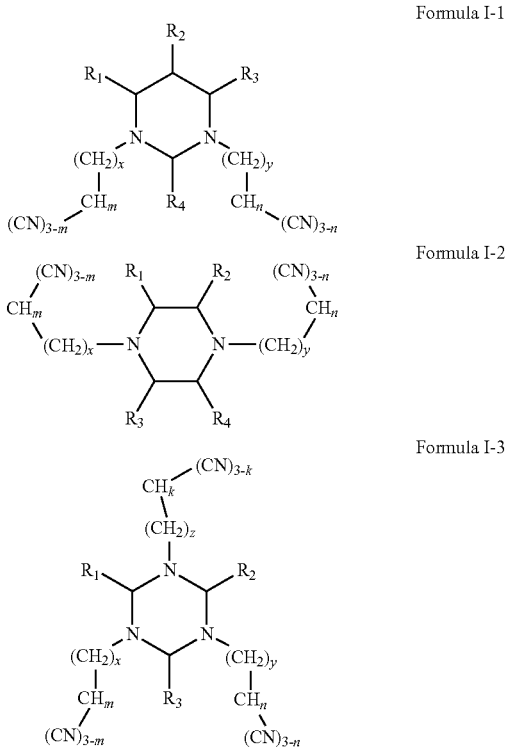

Formula I-1

Formula I-2

Formula I-3

In the Formula I-1, the Formula I-2, and the Formula I-3, $R_1$, $R_2$, $R_3$, and $R_4$ each are independently selected from a hydrogen atom, a halogen atom, a substituted or unsubstituted $C_1$-$C_{12}$ alkyl group, a substituted or unsubstituted $C_1$-$C_{12}$ alkoxy group, a substituted or unsubstituted $C_1$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, or a substituted or unsubstituted $C_2$-$C_{12}$ heterocyclic group, where a substituent group is selected from one or more of a halogen atom, a nitrile group, a $C_1$-$C_6$ alkyl group, a $C_2$-$C_6$ alkenyl group, and a $C_1$-$C_6$ alkoxy group; x, y, and z each are independently selected from integers 0-8; and m, n, and k each are independently selected from integers 0-2.

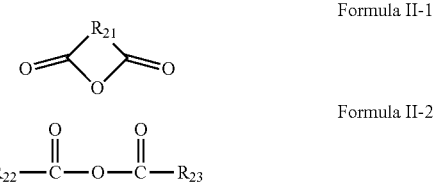

Formula II-1

Formula II-2

In the Formula II-1, $R_{21}$ is selected from a substituted or unsubstituted $C_2$-$C_{12}$ alkyl group, a substituted or unsubstituted $C_2$-$C_{12}$ alkoxy group, a substituted or unsubstituted $C_2$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, or a substituted or unsubstituted $C_2$-$C_{12}$ heterocyclic group, where a substituent group is selected from one or more of a halogen atom, a nitrile group, a $C_1$-$C_6$ alkyl group, a $C_2$-$C_6$ alkenyl group, and a $C_1$-$C_6$ alkoxy group. In the Formula II-2, $R_{22}$ and $R_{23}$ each are independently selected from a hydrogen atom, a substituted or unsubstituted $C_1$-$C_{12}$ alkyl group, a substituted or unsubstituted $C_1$-$C_{12}$ alkoxy group, a substituted or unsubstituted $C_1$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, or a substituted or unsubstituted $C_2$-$C_{12}$ heterocyclic group, where a substituent group is selected from one or more of a halogen atom, a nitrile group, a $C_1$-$C_6$ alkyl group, a $C_2$-$C_6$ alkenyl group, and a $C_1$-$C_6$ alkoxy group.

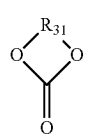

Formula III-1

In the Formula III-1, $R_{31}$ is selected from a halogen substituted $C_1$-$C_6$ alkylene group or a halogen substituted $C_2$-$C_6$ alkenylene group.

According to a second aspect of this application, this application provides an apparatus including the lithium-ion battery as described in the first aspect of this application.

Compared with the prior art, this application provides at least the following beneficial effects:

In this application, a positive active material that contains a metal ion M-doped lithium cobalt oxide material $Li_{x1}Co_{y1}M_{1-y1}O_{2-z1}Q_{z1}$ is used, where the doping element M serves as a framework in the lithium cobalt oxide material. This could reduce lattice deformation of the lithium cobalt oxide material during deep delithiation, delay degradation of bulk structure of the lithium cobalt oxide material, and improve structural stability of the lithium-ion battery when the lithium-ion battery is used at a high voltage greater than 4.2 V.

The electrolyte of this application contains a combination of additives which are the additive A, the additive B, and the additive C. The additive A is a polynitrile six-membered nitrogen-heterocyclic compound with a relatively low oxidation potential, such that a stable complex layer can be formed on a surface of the positive active material during formation of the battery. This could effectively passivate the surface of the positive active material, reduce surface activity of the positive active material, and suppress dissolution of a transition metal into the electrolyte, thereby reducing gas production of the battery while reducing side reactions. The additive B is an anhydride compound, and can absorb moisture in the electrolyte, thereby preventing generation of HF in the electrolyte which causes corrosion and damage to the surface of the positive active material. In addition, the additive B has certain acidity after absorbing moisture, so as to neutralize alkalinity on the surface of the positive active material, and reduce a decomposition effect of an alkaline metal oxide on an organic solvent such as carbonate in the positive active material. The additive C is a halogen substituted cyclic carbonate compound, and can form a uniform, thin, and resilient SEI film on a surface of a negative electrode (especially a surface of a Si-containing negative electrode) to avoid electron conduction between the negative electrode and the electrolyte, thereby effectively reducing side reactions between the negative electrode and the electrolyte and suppressing a continuous increase in negative electrode impedance. In addition, resilience of the protective film could further suppress swelling of the negative electrode (especially a Si-containing negative electrode), and prevent continuous consumption of the electrolyte due to excessive rupture of the SEI film.

The lithium-ion battery of this application has superb cycle performance and storage performance, especially under high-temperature and high-voltage conditions. The apparatus of this application includes the lithium-ion battery as described in the first aspect of this application, and therefore provides at least the same advantages as the lithium-ion battery.

Figure 1:
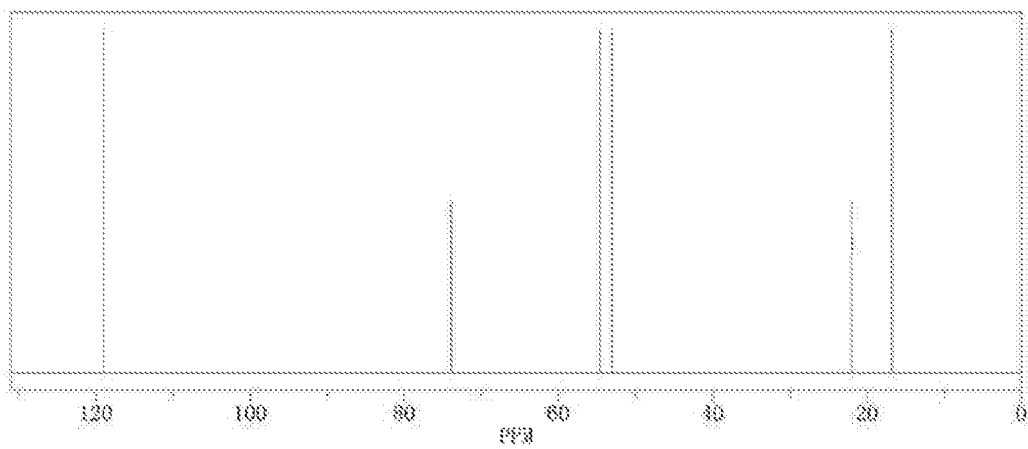
FIG. 1 shows carbon nuclear magnetic resonance spectroscopy of a compound A1.

Reference numerals in the accompanying drawings are described as follows:
1. battery pack;
2. upper cabinet body;
3. lower cabinet body;
4. battery module; and
5. lithium-ion battery.

DESCRIPTION OF EMBODIMENTS

The following describes in detail the lithium-ion battery and apparatus according to this application.

A lithium-ion battery according to a first aspect of this application is described first.

The lithium-ion battery according to this application includes an electrode assembly and an electrolyte. The electrode assembly includes a positive electrode plate, a negative electrode plate, and a separator.

A positive active material of the positive electrode plate includes $Li_{x1}Co_{y1}M_{1-y1}O_{2-z1}Q_{z1}$, where $0.5 \le x1 \le 1.2$, $0.8 \le y1 < 1.0$, $0 \le z1 \le 0.1$, M is selected from one or more of Al, Ti, Zr, Y, and Mg, and Q is selected from one or more of F, Cl, and S. The electrolyte contains an additive A, an additive B, and an additive C. The additive A is selected from one or more of compounds represented by Formula I-1, Formula I-2, and Formula I-3. The additive B is selected from one or more of compounds represented by Formula II-1 and Formula II-2. The additive C is selected from one or more of compounds represented by Formula III-1.

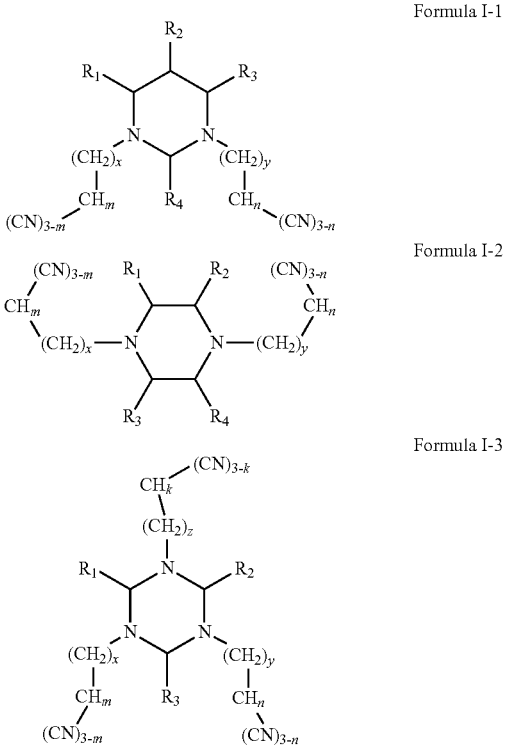

Formula I-1

Formula I-2

Formula I-3

In the Formula I-1, the Formula I-2, and the Formula I-3, $R_1$, $R_2$, $R_3$, and $R_4$ each are independently selected from a hydrogen atom, a halogen atom, a substituted or unsubstituted $C_1$-$C_{12}$ alkyl group, a substituted or unsubstituted $C_1$-$C_{12}$ alkoxy group, a substituted or unsubstituted $C_1$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, or a substituted or unsubstituted $C_2$-$C_{12}$ heterocyclic group, where a substituent group (indicating the case that a substitution occurs in the "substituted or unsubstituted" feature mentioned in this application) is selected from one or more of a halogen atom, a nitrile group, a $C_1$-$C_6$ alkyl group, a $C_2$-$C_6$ alkenyl group, and a $C_1$-$C_6$ alkoxy group; x, y, and z each are independently selected from integers 0-8; and m, n, and k each are independently selected from integers 0-2.

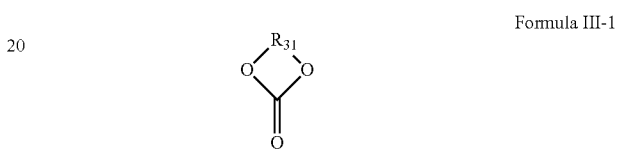

Formula II-1

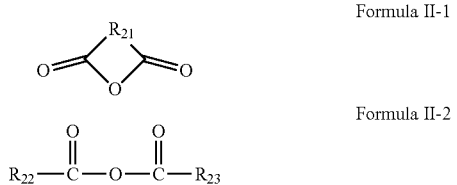

Formula II-2

In the Formula II-1, $R_{21}$ is selected from a substituted or unsubstituted $C_2$-$C_{12}$ alkyl group, a substituted or unsubstituted $C_2$-$C_{12}$ alkoxy group, a substituted or unsubstituted $C_2$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, or a substituted or unsubstituted $C_2$-$C_{12}$ heterocyclic group, where a substituent group (indicating the case that a substitution occurs in the "substituted or unsubstituted" feature mentioned in this application) is selected from one or more of a halogen atom, a nitrile group, a $C_1$-$C_6$ alkyl group, a $C_2$-$C_6$ alkenyl group, and a $C_1$-$C_6$ alkoxy group.

In the Formula II-2, $R_{22}$ and $R_{23}$ each are independently selected from a hydrogen atom, a substituted or unsubstituted $C_1$-$C_{12}$ alkyl group, a substituted or unsubstituted $C_1$-$C_{12}$ alkoxy group, a substituted or unsubstituted $C_1$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, or a substituted or unsubstituted $C_2$-$C_{12}$ heterocyclic group, where a substituent group (indicating the case that a substitution occurs in the "substituted or unsubstituted" feature mentioned in this application) is selected from one or more of a halogen atom, a nitrile group, a $C_1$-$C_6$ alkyl group, a $C_2$-$C_6$ alkenyl group, and a $C_1$-$C_6$ alkoxy group.

Formula III-1

In the Formula III-1, $R_{31}$ is selected from a halogen substituted $C_1$-$C_6$ alkylene group or a halogen substituted $C_2$-$C_6$ alkenylene group.

The lithium-ion battery of this application has superb cycle performance and storage performance, especially under high-temperature and high-voltage conditions. On the one hand, a positive active material that contains a metal ion M-doped lithium cobalt oxide material $Li_{x1}Co_{y1}M_{1-y1}O_{2-z1}Q_{z1}$ is used, where the doping element M serves as a framework in the lithium cobalt oxide material. This could reduce lattice deformation of the lithium cobalt oxide material during deep delithiation, delay degradation of bulk structure of the lithium cobalt oxide material, and improve structural stability of the lithium-ion battery when the lithium-ion battery is used at a high voltage greater than 4.2 V. On the other hand, three additives are added to the electrolyte in this application: the additive A, the additive B, and the additive C. The three additives could synergistically and jointly protect the lithium-ion battery, so that the lithium-ion battery has superb cycle performance and storage performance, especially under high-temperature and high-voltage conditions.

Details are as follows:

(1) The additive A is a polynitrile six-membered nitrogen-heterocyclic compound with a relatively low oxidation potential. Nitrogen atoms in the nitrile groups contain lone pair electrons, which have relatively strong complexation with a transition metal in the positive active material, so that the additive A may be adsorbed on a surface of the positive active material during formation of the battery to form a loose and porous complex layer and effectively passivate the surface of the positive active material. The complex layer could avoid direct contact between the surface of the positive active material and the electrolyte and reduce surface activity of the positive active material, and could further reduce a large quantity of side reactions on the surface of the positive active material and suppress dissolution of a transition metal into the electrolyte. This ensures structural integrity of the positive active material during use of the lithium-ion battery, thereby effectively increasing a capacity retention rate of the lithium-ion battery after cycling at a high voltage, and reducing gas production of the lithium-ion battery during storage at high temperature. In addition, the additive A has a special six-membered nitrogen-heterocyclic structure. A spacing between nitrile groups is closer to that between transition metals on the surface of the positive active material. This could maximize complexation of the nitrile groups and allow more nitrile groups to have a complexation effect. Therefore, compared with a conventional linear nitrile compound, the polynitrile six-membered nitrogen-heterocyclic compound in this application could have a better passivation effect.

(2) The additive B is an anhydride compound, and can absorb moisture in the electrolyte, thereby preventing generation of HF in the electrolyte which causes corrosion and damage to the surface of the positive active material. The additive B has certain acidity after absorbing moisture, so as to neutralize alkalinity on the surface of the positive active material, and reduce a decomposition effect of an alkaline metal oxide on an organic solvent such as carbonate in the positive active material. Therefore, the additive B may also interact with the surface of the positive active material, especially a surface, of the positive active material, that is not protected by the additive A. In addition, although the additive B may also form an acid after absorbing moisture, this part of acid has an extremely small amount and an acidity that is much less than that of HF, so the acid does not corrode or damage the surface of the positive active material.

(3) The additive C is a halogen substituted cyclic carbonate compound, and can form a uniform, thin, and resilient SEI film on a surface of a negative electrode (especially a surface of a Si-containing negative electrode) to avoid electron conduction between the negative electrode and the electrolyte, thereby effectively reducing side reactions between the negative electrode and the electrolyte, and suppressing a continuous increase in negative electrode impedance. In addition, resilience of the protective film could further suppress swelling of the negative electrode (especially a Si-containing negative electrode), and prevent continuous consumption of the electrolyte due to excessive rupture of the SEI film.

In the lithium-ion battery of this application, in the compounds represented by the Formula I-1, the Formula I-2, the Formula I-3, the Formula II-1, and the Formula II-2:

The $C_1$-$C_{12}$ alkyl group may be a chain alkyl group or a cyclic alkyl group, and the chain alkyl group may be a linear alkyl group or a branched chain alkyl group. Hydrogen on a ring of the cyclic alkyl group may be further replaced by an alkyl group. A preferred lower limit of the quantity of carbon atoms in the $C_1$-$C_{12}$ alkyl group is 1, 2, 3, 4, or 5, and a preferred upper limit is 3, 4, 5, 6, 8, 10, or 12. Preferably, a $C_1$-$C_{10}$ alkyl group is selected. More preferably, a $C_1$-$C_6$ chain alkyl group or a $C_3$-$C_8$ cyclic alkyl group is selected. Furthermore preferably, a $C_1$-$C_4$ chain alkyl group or a $C_5$-$C_7$ cyclic alkyl group is selected. Examples of the $C_1$-$C_{12}$ alkyl group may specifically include a methyl group, an ethyl group, an n-propyl group, isopropyl group, an n-butyl group, an isobutyl group, a sec-butyl group, a tert-butyl group, an n-pentyl group, an isopentyl group, a neopentyl group, a hexyl group, a 2-methyl-pentyl group, a 3-methylpentyl group, a 1,1,2-trimethyl-propyl group, a 3,3-dimethyl-butyl group, a heptyl group, a 2-heptyl group, a 3-heptyl group, a 2-methylhexyl group, a 3-methylhexyl group, an isoheptyl group, an octyl group, a nonyl group, and a decyl group.

When the aforementioned $C_1$-$C_{12}$ alkyl group contains oxygen atoms, the $C_1$-$C_{12}$ alkyl group may be a $C_1$-$C_{12}$ alkoxy group. Preferably, a $C_1$-$C_{10}$ alkoxy group is selected. More preferably, a $C_1$-$C_6$ alkoxy group is selected. Furthermore preferably, a $C_1$-$C_4$ alkoxy group is selected. Examples of the C1-C12 alkoxy group may specifically include a methoxy group, an ethoxy group, an n-propoxy group, an isopropoxy group, an n-butoxy group, a sec-butoxy group, a t-butoxy group, an n-pentyloxy group, an isopentyloxy group, a cyclopentyloxy group, and a cyclohexyloxy group.

The $C_2$-$C_{12}$ alkenyl group may be a cyclic alkenyl group or a chain alkenyl group, and the chain alkenyl group may be a linear alkenyl group or a branched alkenyl group. In addition, preferably, the $C_2$-$C_{12}$ alkenyl group has one double bond. A preferred lower limit of the quantity of carbon atoms in the $C_2$-$C_{12}$ alkenyl group is 2, 3, 4, or 5, and a preferred upper limit is 3, 4, 5, 6, 8, 10, or 12. Preferably, a $C_2$-$C_{10}$ alkenyl group is selected. More preferably, a $C_2$-$C_6$ alkenyl group is selected. Furthermore preferably, a $C_2$-$C_5$ alkenyl group is selected. Examples of the $C_2$-$C_{12}$ alkenyl group may specifically include a vinyl group, an allyl group, an isopropenyl group, a pentenyl group, a cyclohexenyl group, a cycloheptenyl group, and a cyclooctenyl group.

The $C_2$-$C_{12}$ alkynyl group may be a cyclic alkynyl group or a chain alkynyl group, and the chain alkynyl group may be a linear alkynyl group or a branched alkynyl group. In addition, preferably, the $C_2$-$C_{12}$ alkynyl group has one triple bond. A preferred lower limit of the quantity of carbon atoms in the $C_2$-$C_{12}$ alkynyl group is 2, 3, 4, or 5, and a preferred upper limit is 3, 4, 5, 6, 8, 10, or 12. Preferably, a $C_2$-$C_{10}$ alkynyl group is selected. More preferably, a $C_2$-$C_6$ alkynyl group is selected. Furthermore preferably, a $C_2$-$C_5$ alkynyl group is selected. Examples of the $C_2$-$C_{12}$ alkynyl group may specifically include an ethynyl group, a propargyl group, an isopropynyl group, a pentynyl group, a cyclohexynyl group, a cycloheptynyl group, and a cyclooctynyl group.

$$-N\begin{matrix}R'\\R''\end{matrix} \text{ or } -\overset{H}{N}-R',$$

The $C_1$-$C_{12}$ amine group may be selected from where R' and R" are selected from the $C_1$-$C_{12}$ alkyl group.

The $C_6$-$C_{26}$ aryl group may be a phenyl group, a phenylalkyl group, a biphenyl group, or a fused ring aromatic hydrocarbon group (for example, a naphthyl group, an anthracenyl group, or a phenanthrenyl group). The biphenyl group and the fused ring aromatic hydrocarbon group may be further substituted with an alkyl group or an alkenyl group. Preferably, a $C_6$-$C_{16}$ aryl group is selected. More preferably, a $C_6$-$C_{14}$ aryl group is selected. Furthermore preferably, a $C_6$-$C_9$ aryl group is selected. Examples of the $C_6$-$C_{26}$ aryl group may specifically include a phenyl group, a benzyl group, a biphenyl group, a p-tolyl group, an o-tolyl group, an m-tolyl group, a naphthyl group, an anthracenyl group, and a phenanthryl group.

A hetero atom in the $C_2$-$C_{12}$ heterocyclic group may be selected from one or more of oxygen, nitrogen, sulfur, phosphorus, and boron, and a heterocyclic ring may be an aliphatic heterocyclic ring or an aromatic heterocyclic ring. Preferably, a $C_2$-$C_{10}$ heterocyclic group is selected. More preferably, a $C_2$-$C_7$ heterocyclic group is selected.

Furthermore preferably, a five-membered aromatic heterocyclic ring, a six-membered aromatic heterocyclic ring, and a benzo heterocyclic ring are selected. Examples of the $C_2$-$C_{12}$ heterocyclic group may specifically include an ethylene oxide group, a propylene oxide group, an ethylene sulfide group, an aziridine group, a β-propiolactone group, a furyl group, a thienyl group, a pyrrolyl group, a thiazolyl group, an imidazolyl group, a pyridyl group, a pyrazinyl group, a pyrimidinyl group, a pyridazinyl group, an indolyl group, and a quinolinyl group.

The halogen atom used as a substituent group may be selected from one or more of a fluorine atom, a chlorine atom, and a bromine atom. Preferably, the halogen atom is a fluorine atom.

(1) Specifically, the compound represented by the Formula I-1 is a polycyanopyrimidine compound.

In the Formula I-1:

Preferably, $R_1$, $R_2$, $R_3$, and $R_4$ each are independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amine group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, or a substituted or unsubstituted $C_2$-$C_{12}$ heterocyclic group. More preferably, $R_1$, $R_2$, $R_3$, and $R_4$ each are independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_3$ alkoxy group, a substituted or unsubstituted $C_1$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group. The substituent group is selected from one or more of halogen atoms.

Preferably, x is selected from integers 0-6; more preferably, is selected from integers 0-4; furthermore preferably, is selected from 0, 1, or 2.

Preferably, y is selected from integers 0-6; more preferably, is selected from integers 0-4; furthermore preferably, is selected from 0, 1, or 2.

Preferably, m is selected from 1 or 2.
Preferably, n is selected from 1 or 2.
Preferably, $R_1$ and $R_3$ are same groups. More preferably, $R_1$, $R_3$, and $R_4$ are all same groups.

Preferably, $R_1$ and $R_3$ are both hydrogen atoms. More preferably, $R_1$, $R_3$, and $R_4$ are all hydrogen atoms.

Preferably, $R_1$, $R_2$, $R_3$, and $R_4$ are all hydrogen atoms; or $R_1$, $R_3$, and $R_4$ are all hydrogen atoms, and $R_2$ is selected from a fluorine atom, a chlorine atom, a bromine atom, a substituted or unsubstituted $C_1$-$C_6$ linear or branched alkyl group, or a substituted or unsubstituted $C_1$-$C_6$ alkoxy group. The substituent group is selected from one or more of halogen atoms. Preferably, the substituent group is selected from a fluorine atom.

Preferably, the compound represented by the Formula I-1 may be specifically selected from one or more of the following compounds, but this application is not limited thereto:

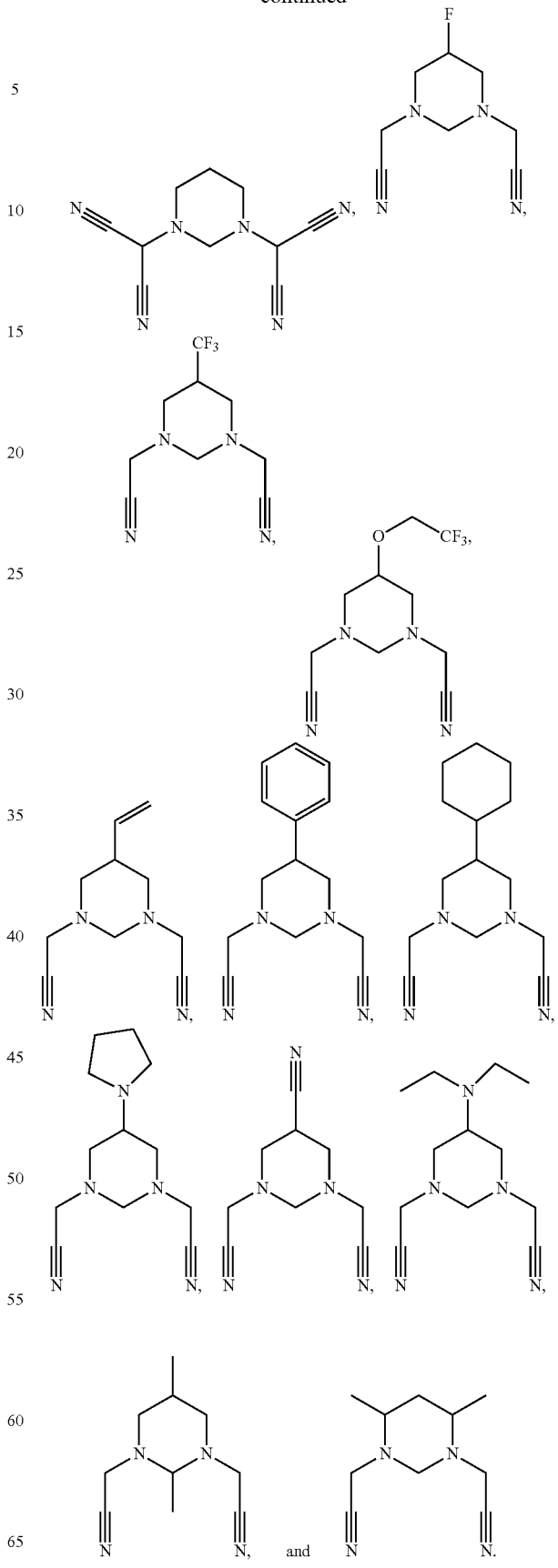

(2) Specifically, the compound represented by the Formula I-2 is a polynitrile piperazine compound.

In the Formula I-2:

Preferably, $R_1$, $R_2$, $R_3$, and $R_4$ each are independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amine group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, or a substituted $C_2$-$C_{12}$ heterocyclic group. More preferably, $R_1$, $R_2$, $R_3$, and $R_4$ each are independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_3$ alkoxy group, a substituted or unsubstituted $C_1$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group. The substituent group is selected from one or more of halogen atoms.

Preferably, x is selected from integers 0-6; more preferably, is selected from integers 0-4; furthermore preferably, is selected from 0, 1, or 2.

Preferably, y is selected from integers 0-6; more preferably, is selected from integers 0-4; furthermore preferably, is selected from 0, 1, or 2.

Preferably, m is selected from 1 or 2.

Preferably, n is selected from 1 or 2.

Preferably, at least two of $R_1$, $R_2$, $R_3$, and $R_4$ are same groups. More preferably, at least three of $R_1$, $R_2$, $R_3$, and $R_4$ are same groups.

Preferably, at least two of $R_1$, $R_2$, $R_3$, and $R_4$ are hydrogen atoms. More preferably, at least three of $R_1$, $R_2$, $R_3$, and $R_4$ are hydrogen atoms.

Preferably, $R_1$, $R_2$, $R_3$, and $R_4$ are all hydrogen atoms; or three of $R_1$, $R_2$, $R_3$, and $R_4$ are hydrogen atoms, and the remaining one is selected from a fluorine atom, a chlorine atom, a bromine atom, a substituted or unsubstituted $C_1$-$C_6$ linear or branched alkyl group, or a substituted or unsubstituted $C_1$-$C_6$ alkoxy group. The substituent group is selected from one or more of halogen atoms. Preferably, the substituent group is selected from a fluorine atom.

Preferably, the compound represented by the Formula I-2 may be specifically selected from one or more of the following compounds, but this application is not limited thereto:

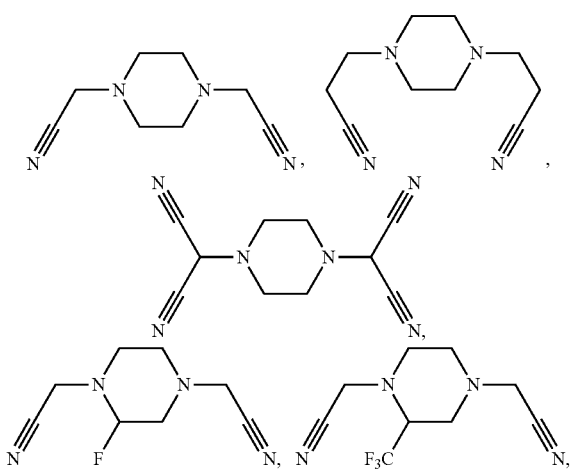

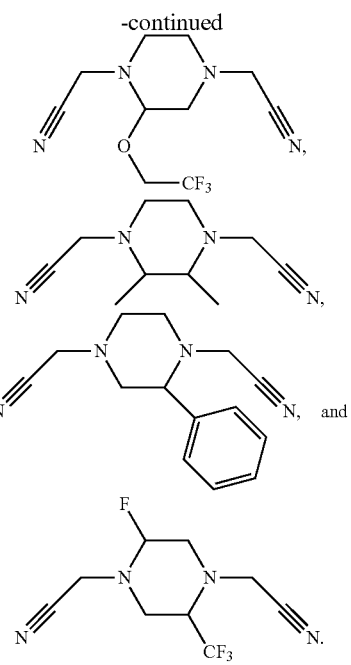

(3) Specifically, the compound represented by the Formula I-3 is a polynitrile s-triazine compound.

In the Formula I-3:

Preferably, $R_1$, $R_2$, and $R_3$ each are independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amine group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, or a substituted or unsubstituted $C_2$-$C_{12}$ heterocyclic group. More preferably, $R_1$, $R_2$, and $R_3$ each are independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxy group, a substituted or unsubstituted $C_1$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group. The substituent group is selected from one or more of halogen atoms.

Preferably, x is selected from integers 0-6; more preferably, is selected from integers 0-4; furthermore preferably, is selected from 0, 1, or 2.

Preferably, y is selected from integers 0-6; more preferably, is selected from integers 0-4; furthermore preferably, is selected from 0, 1, or 2.

Preferably, z is selected from integers 0-6; more preferably, is selected from integers 0-4; furthermore preferably, is selected from 0, 1, or 2.

Preferably, m is selected from 1 or 2.

Preferably, n is selected from 1 or 2.

Preferably, k is selected from 1 or 2.

Preferably, at least two of $R_1$, $R_2$, and $R_3$ are same groups.

Preferably, at least two of $R_1$, $R_2$, and $R_3$ are hydrogen atoms.

Preferably, $R_1$, $R_2$, and $R_3$ are all hydrogen atoms; or two of $R_1$, $R_2$, and $R_3$ are hydrogen atoms, and the remaining one is selected from a fluorine atom, a chlorine atom, a bromine atom, a substituted or unsubstituted $C_1$-$C_6$ linear or branched alkyl group, or a substituted or unsubstituted $C_1$-$C_6$ alkoxy group. The substituent group is selected from one or more of halogen atoms. Preferably, the substituent group is selected from a fluorine atom.

Preferably, the compound represented by the Formula I-3 may be specifically selected from one or more of the following compounds, but this application is not limited thereto:

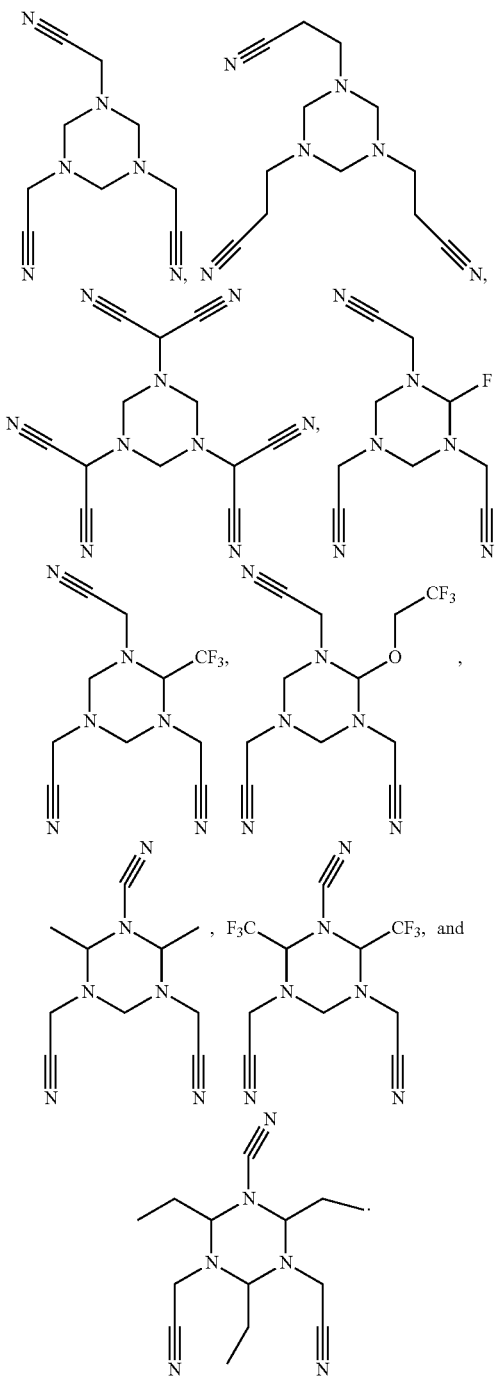

(4) Specifically, the compound represented by the Formula II-1 is cyclic carboxylic acid anhydride.

In the Formula II-1:

Preferably, $R_{21}$ is selected from a substituted or unsubstituted $C_2$-$C_6$ linear or branched alkyl group, a substituted or unsubstituted $C_5$-$C_9$ cyclic alkyl group, a substituted or unsubstituted $C_2$-$C_6$ alkoxy group, a substituted or unsubstituted $C_2$-$C_6$ amine group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, or a substituted or unsubstituted $C_2$-$C_{12}$ heterocyclic group. More preferably, $R_{21}$ is selected from a substituted or unsubstituted $C_2$-$C_3$ linear or branched alkyl group, a substituted or unsubstituted $C_5$-$C_7$ cyclic alkyl group, a substituted or unsubstituted $C_2$-$C_3$ alkoxy group, a substituted or unsubstituted $C_2$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group. The substituent group is selected from one or more of halogen atoms.

Preferably, the compound represented by the Formula II-1 may be selected from one or more of succinic anhydride, glutaric anhydride, maleic anhydride, and phthalic anhydride.

(5) Specifically, the compound represented by the Formula II-2 is chain carboxylic acid anhydride.

In the Formula II-2:

Preferably, $R_{22}$ and $R_{23}$ each are independently selected from a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amine group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, or a substituted or unsubstituted $C_2$-$C_{12}$ heterocyclic group. More preferably, $R_{22}$ and $R_{23}$ each are independently selected from a substituted or unsubstituted $C_2$-$C_3$ linear or branched alkyl group, a substituted or unsubstituted $C_5$-$C_7$ cyclic alkyl group, a substituted or unsubstituted $C_2$-$C_3$ alkoxy group, a substituted or unsubstituted $C_2$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group. The substituent group is selected from one or more of halogen atoms.

Preferably, the compound represented by the Formula II-2 may be selected from one or more of acetic anhydride, propionic anhydride, butyric anhydride, and valeric anhydride.

In the lithium-ion battery of this application, the compound represented by the Formula III-1 is a halogen substituted cyclic carbonate compound.

The halogen atom used for substitution of an alkylene group or an alkenylene group may be selected from one or more of a fluorine atom, a chlorine atom, and a bromine atom. Preferably, the halogen atom is a fluorine atom.

In the Formula III-1, preferably, $R_{21}$ is selected from a halogen substituted $C_2$-$C_4$ alkylene group or a halogen substituted $C_2$-$C_4$ alkenylene group.

Preferably, the additive C may be specifically selected from one or more of fluoroethylene carbonate (FEC), fluoropropylene carbonate (FPC), trifluoropropylene carbonate (TFPC), and trans- or cis-4,5-difluoro-1,3-dioxolane-2-ketone (DFEC).

In the lithium-ion battery of this application, preferably, mass percent of the additive A in the electrolyte is 0.1%-10%. If the amount of the additive A is too low, improvement made by the additive A to the electrolyte is not obvious; if the amount of the additive A is too high, the complex layer formed by the additive A adsorbed on the surface of the positive active material would be too thick and dense, affecting diffusion and migration of lithium ions, and greatly increasing positive electrode impedance. In addition, excessively high amount of the additive A further causes an increase in overall viscosity of the electrolyte and a decrease in an ionic conductivity, and therefore, affects performance of the lithium-ion battery.

More preferably, mass percent of the additive A in the electrolyte is 0.1%-6%. Furthermore preferably, mass percent of the additive A in the electrolyte is 0.1%-3.5%.

In the lithium-ion battery of this application, preferably, mass percentage of the additive B in the electrolyte is 0.1%-10%. The additive B can effectively absorb moisture in the electrolyte, thereby effectively suppressing formation of HF and preventing the surface of the positive active material from being corroded. In addition, the additive B has certain acidity after absorbing moisture, so as to neutralize alkalinity on the surface of the positive active material, and reduce a decomposition effect of an alkaline metal oxide on an organic solvent such as carbonate in the positive active material. This could effectively improve storage performance of the lithium-ion battery. However, the percent of the additive B needs to be moderate. If the percent of the additive B is too low, moisture in the electrolyte could not be completely absorbed, thus failing to remove moisture and suppress generation of HF; if the percent of the additive B is too high, a product produced by the additive B by absorbing moisture would be excessively acidic, also imposing certain corrosive effect on the positive active material. An upper limit of a percent range of the additive B may be any one selected from 10%, 9%, 8%, 7%, 6%, 5%, 4.5%, 4%, 3.5%, 3%, 2.5%, 2%, 1.5%, 1%, or 0.8%, and a lower limit of the percent range of the additive B may be any one selected from 0.1%, 0.2%, 0.3%, 0.4%, 0.5%, 0.6%, 0.7%, 0.8%, 0.9%, 1.0%, or 1.2%.

More preferably, mass percent of the additive B in the electrolyte is 0.1%-5%.

In the lithium-ion battery of this application, preferably, mass percent of the additive C in the electrolyte is 0.1%-30%. The additive C is mainly used to form a film at the negative electrode, and can effectively suppress side reactions on the surface of the negative electrode. Because the film formed by the additive C is uniform and resilient, the additive C is especially suitable for a Si-containing negative electrode system. If the amount of the additive C is too low, a film formed by the additive C at the negative electrode would be insufficient in both thickness and strength, and therefore side reactions on the surface of the negative electrode and swelling of the negative electrode could not be effectively suppressed; if the percent of the additive C is too high, an excessively thick film is likely to be formed at the negative electrode, significantly increasing negative electrode impedance, and further affecting cycle performance of the lithium-ion battery. In addition, due to relatively poor thermal stability and easy decomposition of the additive C, excessively high amount also causes massive gas production of the lithium-ion battery, resulting in bubbles and a fracturing bridge phenomenon of the electrolyte inside the battery, and further increasing battery impedance. An upper limit of a percent range of the additive C may be any one selected from 30%, 28%, 25%, 22%, 19%, 16%, 15%, 14%, 13%, 12%, 11%, 10%, 9%, 8%, 7%, 6%, or 5%, and a lower limit of the percent range of the additive C may be any one selected from 0.1%, 0.2%, 0.3%, 0.4%, 0.5%, 0.6%, 0.7%, 0.8%, 0.9%, 1%, 2%, 3%, 4%, or 5%.

More preferably, mass percent of the additive C in the electrolyte is 5%-15%.

In the lithium-ion battery of this application, the electrolyte further includes an organic solvent and an electrolyte salt.

A type of the organic solvent used in the electrolyte in embodiments of this application is not particularly limited. Preferably, the organic solvent may include a cyclic carbonate and a chain carbonate, and could further improve cycle performance and storage performance of the lithium-ion battery under high-temperature and high-voltage conditions. In addition, it is easy to adjust a conductivity of the electrolyte to a suitable range, thus helping the additive A, the additive B, and the additive C achieve a better film-forming effect.

The organic solvent used in the electrolyte in this embodiment of this application may further include a carboxylic acid ester. To be specific, the organic solvent in this application may include a mixture of a cyclic carbonate, a chain carbonate, and a carboxylic acid ester. The carboxylic acid ester is characterized by large dielectric constant and low viscosity, and could effectively prevent association of lithium ions and anions in the electrolyte. In addition, the carboxylic acid ester is more advantageous than the cyclic carbonate and the chain carbonate in terms of ion conduction. Especially at low temperature, the carboxylic acid ester could ensure good ion conduction for the electrolyte.

Based on total mass of the organic solvent, mass percent of the cyclic carbonate may be 15%-55%, preferably 25%-50%; mass percent of the chain carbonate may be 15%-74%, preferably 25%-70%; and mass percent of the carboxylic acid ester may be 0.1%-70%, preferably 5%-50%.

Specifically, the cyclic carbonate may be selected from one or more of an ethylene carbonate, a propylene carbonate, a 1,2-butylene carbonate, and a 2,3-butanediol carbonate. More preferably, the cyclic carbonate may be selected from one or more of an ethylene carbonate and a propylene carbonate.

Specifically, the chain carbonate may be one or more asymmetric chain carbonates selected from an ethyl methyl carbonate, a methyl propyl carbonate, a methyl isopropyl carbonate, a methyl butyl carbonate, and an ethyl propyl carbonate; the chain carbonate may also be one or more symmetric chain carbonates selected from a dimethyl carbonate, a diethyl carbonate, a dipropyl carbonate, and a dibutyl carbonate; the chain carbonate may also be a mixture of the asymmetric chain carbonate and the symmetric chain carbonate.

Specifically, the carboxylic acid ester may be selected from one or more of methyl pivalate, ethyl pivalate, propyl pivalate, butyl pivalate, methyl butyrate, ethyl butyrate, propyl butyrate, butyl butyrate, methyl propionate, ethyl propionate, propyl propionate, butyl propionate, methyl acetate, ethyl acetate, propyl acetate, and butyl acetate.

The electrolyte salt used in this embodiment of this application may be the following enumerated lithium salts as appropriate.

[Li salts—category 1]: This may include, as appropriate, one or more "Lewis acid and LiF complex salts" selected from $LiPF_6$, $LiBF_4$, $LiAsF_6$, $LiSbF_6$, $LiPF_4(CF_3)_2$, $LiPF_3(C_2F_5)_3$, $LiPF_3(CF_3)_3$, $LiPF_3(iso-C_3F_7)_3$, and $LiPF_5(iso-C_3F_7)$, preferably selected from $LiPF_6$, $LiBF_4$, or $LiAsF_6$, more preferably selected from $LiPF_6$ or $LiBF_4$.

[Li salts—category 2]: This may include, as appropriate, one or more "imine or methylated lithium salts" selected from $(CF_2)_2(SO_2)_2NLi$ (cyclic), $(CF_2)_3(SO_2)_2NLi$ (cyclic), and $LiC(SO_2CF_3)_3$.

[Li salts—category 3]: This may include, as appropriate, one or more "lithium salts containing an $S(=O)O$ structure" selected from $LiSO_3F$, $LiCF_3SO_3$, $CH_3SO_4Li$, $C_2H_5SO_4Li$, $C_3H_7SO_4Li$, lithium trifluoro ((methanesulfonyl) oxy) borate (LiTFMSB), and lithium pentafluoro ((methanesulfonyl) oxy) phosphate (LiPFMSP), preferably selected from $LiSO_3F$, $CH_3SO_4Li$, $C_2H_5SO_4Li$, or LiTFMSB.

[Li salts—category 4]: This may include, as appropriate, one or more "lithium salts containing a $P=O$ or $Cl=O$ structure" selected from $LiPO_2F_2$, $Li_2PO_3F$, and $LiClO_4$, preferably selected from $LiPO_2F_2$ or $Li_2PO_3F$.

[Li salts—category 5]: This may include, as appropriate, one or more "lithium salts using oxalate ligands as positive ions" selected from lithium bis[oxalate-O, O']borate (LiBOB), lithium difluoro[oxalate-O, O']borate, lithium difluorobis[oxalate-O, O']phosphate (LiPFO), and lithium tetrafluoro[oxalate-O, O'] phosphate, preferably selected from LiBOB or LiPFO.

The foregoing lithium salts may be used alone or in combination. Preferably, the lithium salt is selected from one or more of $LiPF_6$, $LiPO_2F_2$, $Li_2PO_3F$, $LiBF_4$, $LiSO_3F$, lithium trifluoro((methanesulfonyl)oxy)borate (LiTFMSB), lithium bis[oxalate-O, O']borate (LiBOB), lithium difluorobis [oxalate-O, O']phosphate (LiPFO), and lithium tetrafluoro[oxalate-O, O']phosphate. More preferably, the lithium salt is selected from one or more of $LiPF_6$, $LiBF_4$, $LiSO_3F$, lithium trifluoro((methanesulfonyl)oxy)borate (LiTFMSB), $LiPO_2F_2$, lithium bis[oxalate-O, O']borate (LiBOB), and lithium difluorobis[oxalate-O, O']phosphate (LiPFO). Furthermore preferably, the lithium salt is $LiPF_6$.

In the lithium-on battery of this application, concentration of the electrolyte salt is not particularly limited, and may be adjusted according to actual needs.

In the lithium-ion battery of this application, preferably, the conductivity at 25° C. of the electrolyte is 4 mS/cm-12 mS/cm.

In the lithium-ion battery of this application, a preparation method for the electrolyte is not limited, and the electrolyte may be prepared according to a method for a conventional electrolyte.

In the lithium-ion battery of this application, $Li_{x1}Co_{y1}M_{1-y1}O_{2-z1}Q_{z1}$ may be specifically selected from one or more of $LiCo_{0.9}Zr_{0.1}O_2$, $LiCo_{0.9}Ti_{0.1}O_2$, $Li_{1.05}Co_{0.8}Mg_{0.2}O_2$,
$Li_{1.01}Co_{0.98}Mg_{0.01}Ti_{0.005}Al_{0.005}O_2$,
$Li_{1.05}Co_{0.98}Mg_{0.005}Zr_{0.005}Ti_{0.01}O_{1.9}F_{0.1}$,
$Li_{1.1}Co_{0.95}Mg_{0.01}Zr_{0.01}Al_{0.03}O_2$,
$Li_{1.04}Co_{0.95}Mg_{0.02}Zr_{0.03}O_{1.95}F_{0.05}$,
$Li_{1.06}Co_{0.96}Mg_{0.02}Ti_{0.02}O_2$,
$Li_{1.08}Co_{0.97}Mg_{0.01}Zr_{0.01}Al_{0.01}O_{1.9}S_{0.1}$,
$Li_{1.09}Co_{0.98}Mg_{0.01}Ti_{0.005}Al_{0.005}O_2$,
$L_{1.085}Co_{0.98}Zr_{0.01}Ti_{0.005}Al_{0.005}O_{1.9}Cl_{0.1}$,
$Li_{1.03}Co_{0.96}Mg_{0.01}Zr_{0.01}Ti_{0.01}Al_{0.01}O_2$,
$Li_{1.04}Co_{0.97}Zr_{0.01}Al_{0.02}O_{1.9}F_{0.1}$,
$L_{1.07}Co_{0.97}Zr_{0.01}Ti_{0.01}Al_{0.01}O_{1.9}S_{0.1}$,
$L_{1.02}Co_{0.96}Mg_{0.02}Zr_{0.012}Ti_{0.005}O_{1.9}S_{0.1}$,
$Li_{1.03}Co_{0.98}Ti_{0.01}Al_{0.01}O_{1.9}Cl_{0.1}$,
$Li_{1.05}Co_{0.97}Mg_{0.01}Zr_{0.01}Al_{0.01}O_{1.9}Cl_{0.1}$,
$Li_{1.04}Co_{0.95}Zr_{0.02}Ti_{0.03}O_{1.9}F_{0.1}$,
$Li_{1.09}Co_{0.97}Mg_{0.02}Ti_{0.01}O_{1.95}F_{0.05}$,
$L_{1.03}Co_{0.95}Mg_{0.03}Ti_{0.02}O_{1.9}S_{0.1}$, and
$L_{1.04}Co_{0.97}Zr_{0.01}Ti_{0.01}Al_{0.01}O_{1.9}S_{0.1}$.

In the lithium-ion battery of this application, the positive active material may further include one or more of a lithium nickel oxide, a lithium manganese oxide, a lithium nickel manganese oxide, a lithium nickel cobalt manganese oxide, a lithium nickel cobalt aluminum oxide, and a compound obtained by adding another transition metal or non-transition metal to any of the foregoing oxide.

In the lithium-ion battery of this application, the positive electrode plate further includes a binder and a conductive agent. A positive slurry containing the positive active material, the binder, and the conductive agent is applied onto a positive current collector, and then dried to give the positive electrode plate. Types and amounts of the conductive agent and the binder are not specifically limited, and may be selected according to actual needs. A type of the positive current collector is not specifically limited either, and may be selected according to actual needs. Preferably, the positive current collector may be an aluminum foil.

In the lithium-ion battery of this application, a negative active material in the negative electrode plate may include one or more of Si, $SiO_{x2}$, a Si/C composite material, and Si alloy, and $0<x2\leq2$. The negative active material may further include one or more of soft carbon, hard carbon, artificial graphite, natural graphite, lithium titanate, and a metal that can form an alloy with lithium.

In the lithium-ion battery of this application, the negative electrode plate further includes a binder and a conductive agent. A negative slurry containing the negative active material, the binder, and the conductive agent is applied onto a negative current collector, and then dried to give the negative electrode plate. Types and amounts of the conductive agent and the binder are not specifically limited, and may be selected according to actual needs. A type of the negative current collector is not specifically limited either, and may be selected according to actual needs. Preferably, the positive current collector may be a copper foil.

In the lithium-ion battery of this application, the separator is disposed between the positive electrode plate and the negative electrode plate, and has an effect of separation. A specific type of the separator is not specifically limited, and the separator may be, but not limited to, any separator materials used in existing lithium-ion batteries, for example, polyethylene, polypropylene, polyvinylidene fluoride, and a multilayer composite film thereof.

In the lithium-ion battery of this application, an end-of-charge voltage of the lithium-ion battery is not less than 4.2 V, that is, the lithium-ion battery may be used at a high voltage of not less than 4.2 V. Preferably, the end-of-charge voltage of the lithium-ion battery is not less than 4.35 V.

The lithium-ion battery of this application may be either a hard-shell lithium-ion battery or a soft-package lithium-ion battery. Preferably, a metal hard shell is used for the hard-shell lithium-ion battery. Preferably, a packaging bag is used as a battery housing of the soft-package lithium-ion battery. The packaging bag typically includes an accommodating portion and a sealing portion. The accommodating portion is configured to accommodate the electrode assembly and the electrolyte, and the sealing portion is configured to seal the electrode assembly and the electrolyte. The electrolyte of this application achieves more obvious improvement on performance of the soft-package lithium-ion battery, because the soft-package lithium-ion battery per se is prone to swelling during use, whereas the electrolyte of this application could greatly reduce gas production of the battery and prevent from shortening the life of the battery due to the swelling of the soft-package lithium-ion battery.

In the lithium-ion battery of this application, the additive A may be synthesized by using the following method.

(1) Preparation of the Compound Represented by the Formula I-1

A reaction scheme is as follows:

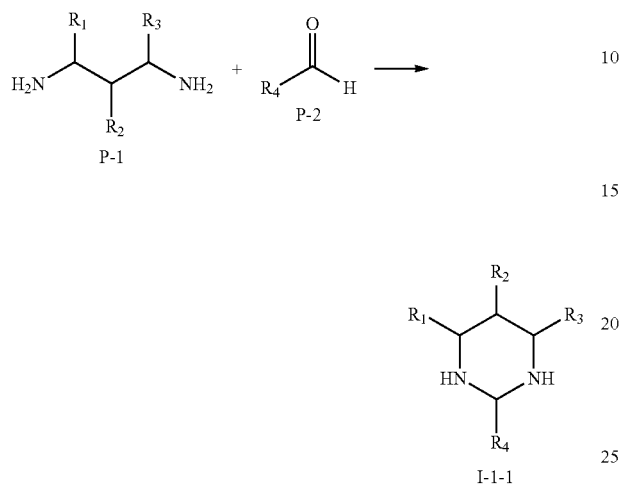

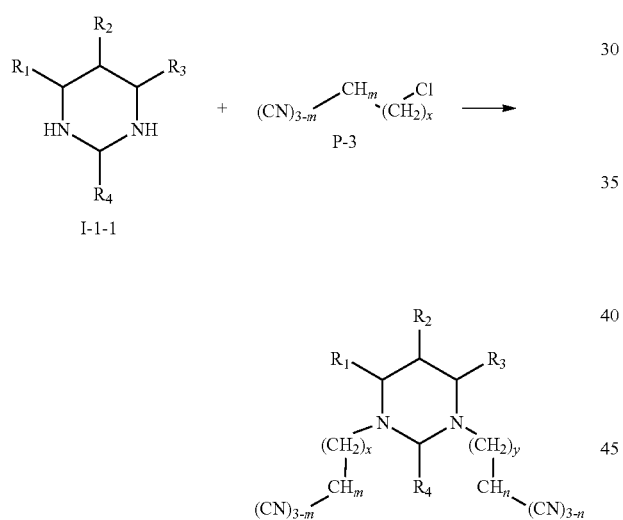

A specific preparation process includes the following steps:

Adding aqueous solution P-2 with a concentration of 30%-40% dropwise to a raw material P-1 within 20 min-60 min with quickly stirring. After the dropwise addition is completed, quickly stirring the solution for 15 h-30 h. Stirring the solution in an oil bath at 70° C.-90° C. under reflux for 3 h-5 h to obtain a colorless, fuming, and viscous liquid intermediate product I-1-1. Then adding $K_2CO_3$, KI, and anhydrous acetonitrile, and quickly stirring them to form a solid-liquid mixture. Quickly adding a raw material P-3 at 40° C.-60° C., then stirring them for 10 h-20 h, and cooling the mixture to room temperature. Then performing separation and purification to obtain the compound represented by the Formula I-1.

(2) Preparation of the Compound Represented by the Formula I-2

A reaction scheme is as follows:

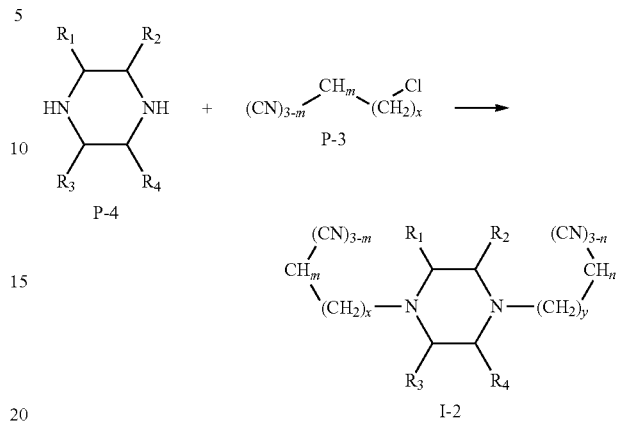

A specific preparation process includes the following steps:

Mixing anhydrous sodium carbonate, a raw material P-4, and a raw material P-3 in absolute ethanol, and stirring them for 2 h-5 h for a reaction. Repeatedly washing with hot ethanol for a plurality of times to obtain a crude product, and performing recrystallization to obtain the compound represented by the Formula I-2.

(3) Preparation of the Compound Represented by the Formula I-3

A reaction scheme is as follows:

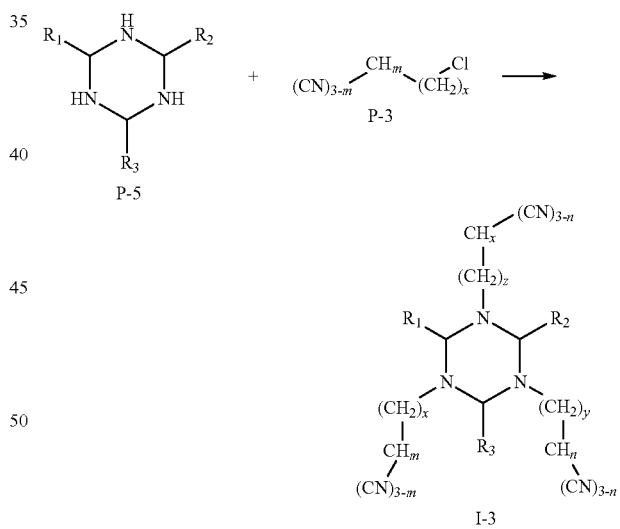

A specific preparation process includes the following steps:

Mixing anhydrous sodium carbonate, a raw material P-5, and a raw material P-3 in absolute ethanol, and stirring them for 2 h-5 h for a reaction. Repeatedly washing with hot ethanol for a plurality of times to obtain a crude product, and performing recrystallization to obtain the compound represented by the Formula I-3.

Then a lithium-ion battery according to a second aspect of this application is described.

The lithium-ion battery according to the second aspect of this application includes an electrode assembly and the electrolyte according to the first aspect of this application. The electrode assembly includes a positive electrode plate, a negative electrode plate, and a separator.

In the lithium-ion battery in the second aspect of this application, a positive active material of the positive electrode plate includes $Li_{x1}Co_{y1}M_{1-y1}O_{2-z1}Q_{z1}$, where $0.5 \le x1 \le 1.2$, $0.8 \le y1 < 1.0$, $0 \le z1 \le 0.1$, M is selected from one or more of Al, Ti, Zr, Y, and Mg, and Q is selected from one or more of F, Cl, and S.

In some embodiments, the lithium-ion battery may include an outer package for encapsulating the positive electrode plate, the electrode plate, and an electrolyte medium. In an example, the positive electrode plate, the negative electrode plate, and the separator may be laminated or wound to form an electrode assembly of a laminated structure or an electrode assembly of a wound structure, and the electrode assembly is encapsulated in an outer package. The electrolyte medium may be an electrolyte, which infiltrates in the electrode assembly. There may be one or more electrode assemblies in the lithium-ion battery, depending on needs.

In some embodiments, the outer package of the lithium-ion battery may be a soft package, for example, a soft bag. A material of the soft package may be plastic, for example, may include one or more of polypropylene PP, polybutylene terephthalate PBT, polybutylene succinate PBS, and the like. Alternatively, the outer package of the lithium-ion battery may be a hard shell, for example, an aluminum shell.

Figure 4:
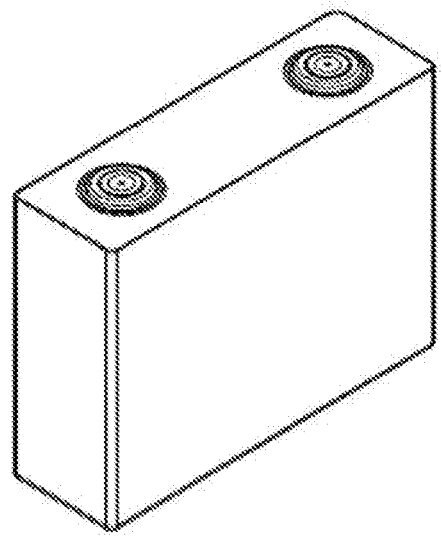
FIG. 4 is a schematic diagram of an embodiment of a lithium-ion battery.

Shape of the lithium-ion battery in this application is not particularly limited, and may be of a cylindrical, square, or any other shape. FIG. 4 shows an example of a lithium-ion battery 5 of a square structure.

In some embodiments, lithium-ion batteries may be assembled into a battery module, and the battery module may include a plurality of lithium-ion batteries. A specific quantity may be adjusted based on application and capacity of the battery module.

Figure 5:
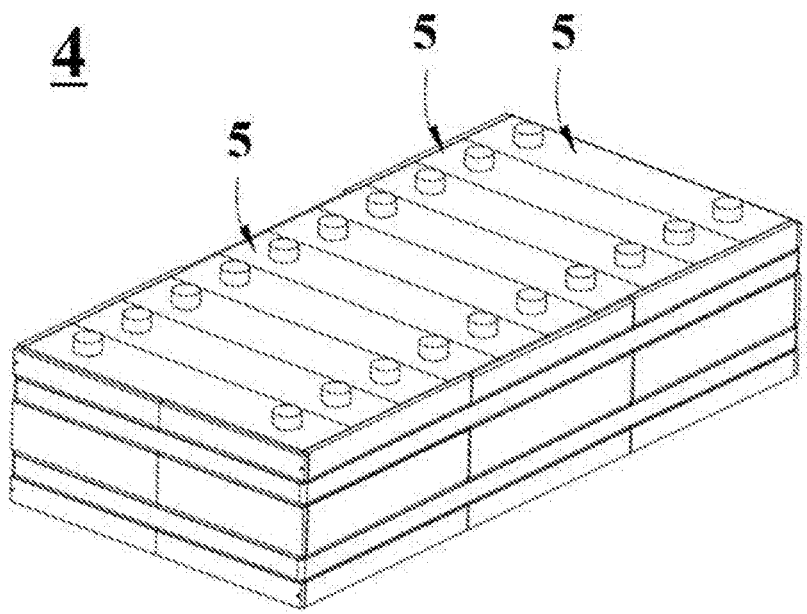
FIG. 5 is a schematic diagram of an embodiment of a battery module.

FIG. 5 shows an example of a battery module 4. Referring to FIG. 5, in the battery module 4, a plurality of lithium-ion batteries 5 may be sequentially arranged along a length direction of the battery module 4; or certainly, may be arranged in any other manner. Further, the plurality of lithium-ion batteries 5 may be fixed by using fasteners.

Optionally, the battery module 4 may further include a housing with an accommodating space, and the plurality of lithium-ion batteries 5 are accommodated in the accommodating space.

In some embodiments, battery modules may be further assembled into a battery pack, and the quantity of battery modules included in the battery pack may be adjusted based on application and capacity of the battery pack.

Figure 6:
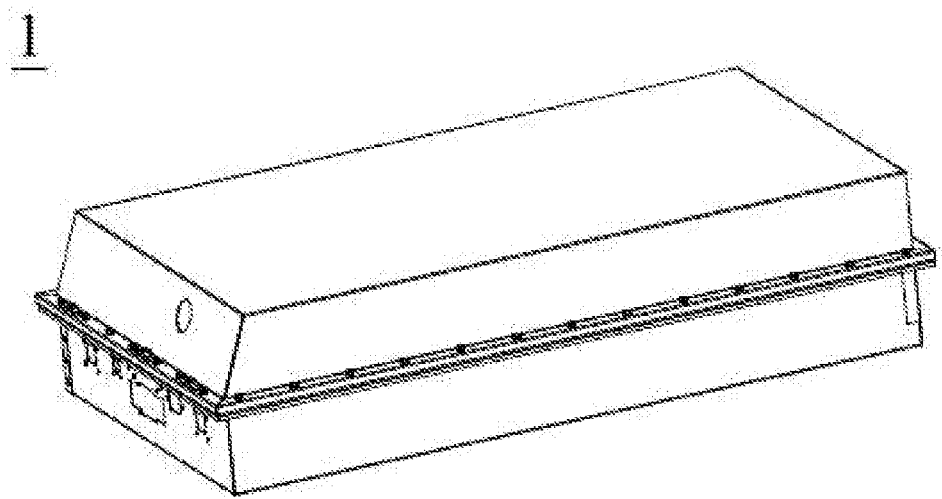
FIG. 6 is a schematic diagram of an embodiment of a battery pack.
Figure 7:
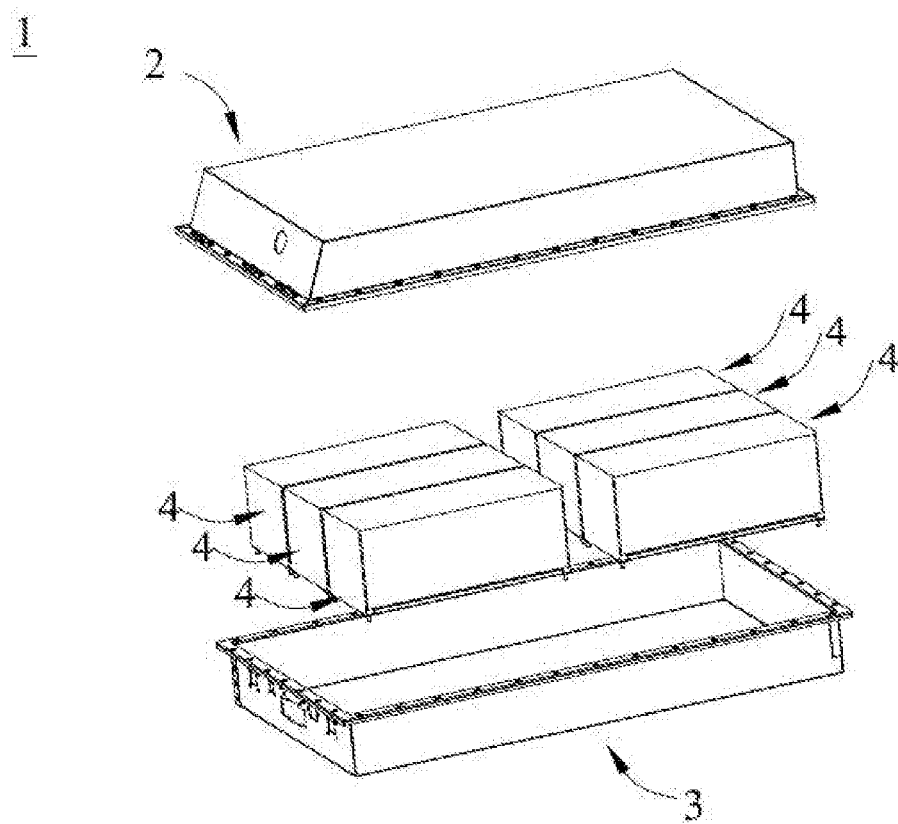
FIG. 7 is an exploded diagram of FIG. 6.

FIG. 6 and FIG. 7 show an example of a battery pack 1. Referring to FIG. 6 and FIG. 7, the battery pack 1 may include a battery cabinet and a plurality of battery modules 4 disposed in the battery cabinet. The battery cabinet includes an upper cabinet body 2 and a lower cabinet body 3. The upper cabinet body 2 can cover the lower cabinet body 3 and form an enclosed space for accommodating the battery modules 4. The plurality of battery modules 4 may be arranged in the battery cabinet in any manner.

An apparatus according to a second aspect of this application is described next.

A second aspect of this application provides an apparatus. The apparatus includes the lithium-ion battery in the first aspect of this application, and the lithium-ion battery supplies power to the apparatus. The apparatus may be, but not limited to, a mobile device (for example, a mobile phone or a notebook computer), an electric vehicle (for example, a full electric vehicle, a hybrid electric vehicle, a plug-in hybrid electric vehicle, an electric bicycle, an electric scooter, an electric golf vehicle, or an electric truck), an electric train, a ship, a satellite, an energy storage system, and the like.

A lithium-ion battery, a battery module, or a battery pack may be selected for the apparatus according to requirements for using the apparatus.

Figure 8:
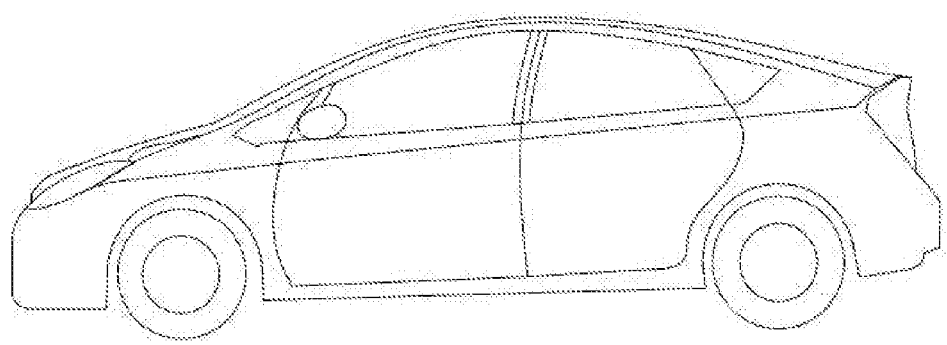
FIG. 8 is a schematic diagram of an embodiment of an apparatus using a lithium-ion battery as a power source.

FIG. 8 shows an example of an apparatus. The apparatus is a full electric vehicle, a hybrid electric vehicle, a plug-in hybrid electric vehicle, or the like. To meet a requirement of the apparatus for high power and a high energy density of a lithium-ion battery, a battery pack or a battery module may be used.

In another example, the apparatus may be a mobile phone, a tablet computer, a notebook computer, or the like. The apparatus is generally required to be light and thin, and may use a lithium-ion battery as its power source.

To make the objectives, technical solutions, and beneficial technical effects of this application clearer, this application is further described below in detail with reference to embodiments. It should be understood that the embodiments described in this specification are merely intended to explain this application, but not to limit this application. Formulations, proportions, and the like of the embodiments may be adjusted as appropriate to actual conditions without substantial effect on results.

All reagents, materials, and instruments that are used in Examples and Comparative Examples are commercially available unless otherwise specified. Specific synthesis processes of additives A1, A2, and A3 are as follows. Other types of additives A may be synthesized according to similar methods.

Synthesis of the Additive A1:

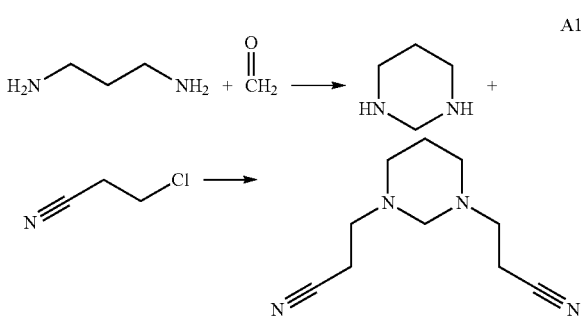

37% formaldehyde aqueous solution was added dropwise to 1,3-propanediamine within 0.5 h with quick stirring. After the completion of dropwise addition, the solution was still quickly stirred for 20 h. Then the solution was stirred in an oil bath at 80° C. reflux for 4 h to obtain intermediate product hexahydropyrimidine as a colorless, fuming, and viscous liquid. $K_2CO_3$, KI, and anhydrous acetonitrile were added, followed by quick stirring to form a solid-liquid mixture. Then β-chloropropionitrile was added at 60° C. within 0.5 h. The mixture was stirred for 17 h, and cooled to room temperature. Then the mixture was subjected to separation and purification to obtain A1. Carbon nuclear magnetic resonance spectroscopy was shown in FIG. 1.

Synthesis of the Additive A2:

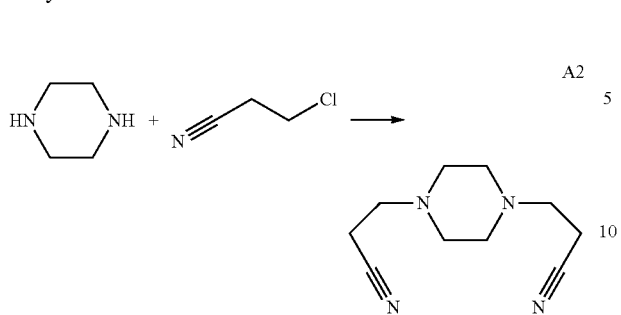

Figure 2:
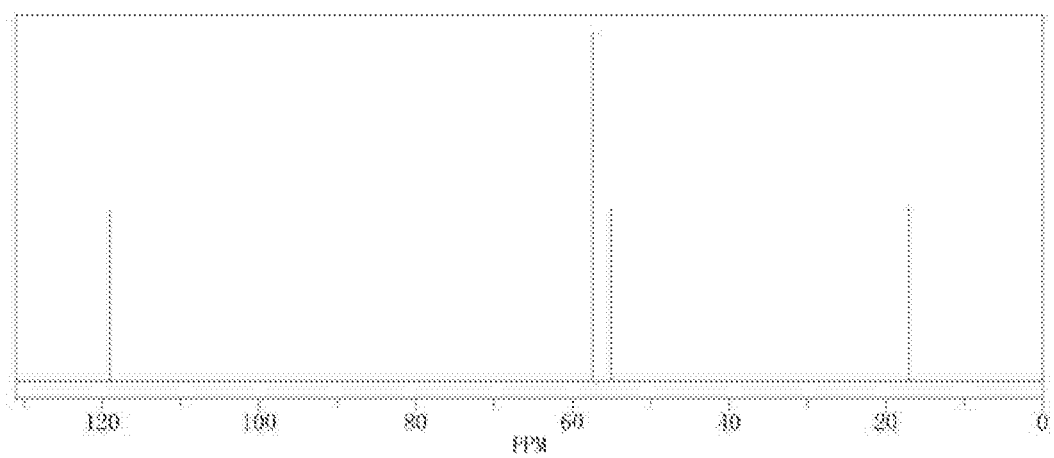
FIG. 2 shows carbon nuclear magnetic resonance spectroscopy of a compound A2.

Anhydrous sodium carbonate, piperazine, and β-chloropionitrile were mixed in absolute ethanol, and stirred for 4 h for reaction. The mixture was repeatedly washed with hot ethanol for a plurality of times to obtain a crude product, and subjected to recrystallization to obtain A2. Carbon nuclear magnetic resonance spectroscopy was shown in FIG. 2.

Synthesis of the Additive A3:

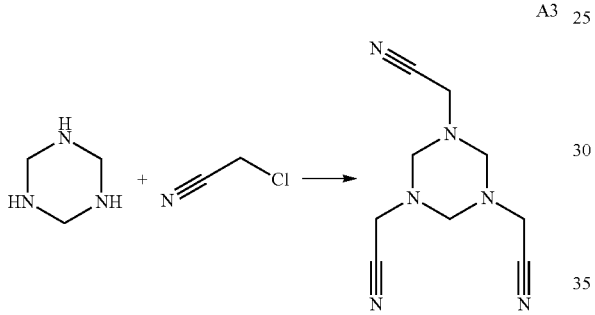

Figure 3:
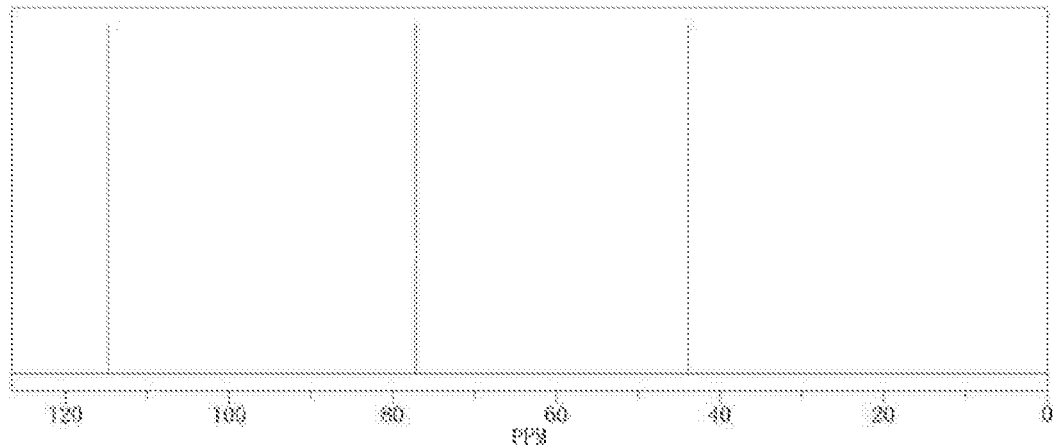
FIG. 3 shows carbon nuclear magnetic resonance spectroscopy of a compound A3.

Anhydrous sodium carbonate, 1,3,5-s-triazine, and chloroacetonitrile were mixed in absolute ethanol, and stirred for 4 h for reaction. The mixture was repeatedly washed with hot ethanol for a plurality of times to obtain a crude product, and subjected to recrystallization to obtain A3. Carbon nuclear magnetic resonance spectroscopy was shown in FIG. 3.

To make the invention objectives, technical solutions, and beneficial technical effects of this application clearer, this application is further described below in detail with reference to embodiments. It should be understood that the embodiments described in this specification are merely intended to explain this application, but not to limit this application. Formulations, proportions, and the like of the embodiments may be adjusted as appropriate to actual conditions without substantial effect on results.

All reagents, materials, and instruments that are used in Examples and Comparative Examples are commercially available unless otherwise specified. Specific synthesis processes of additives A1, A2, and A3 are as follows. Other types of additives A may be synthesized according to similar methods.

Synthesis of the Additive A1:

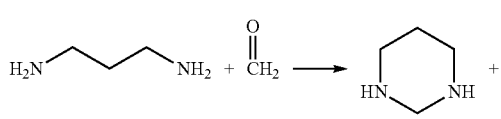

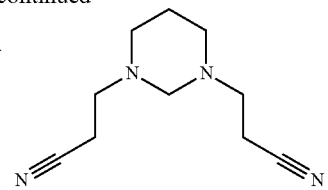

37% formaldehyde aqueous solution was added dropwise to 1,3-propanediamine within 0.5 h with quick stirring the solution. After the completion of dropwise addition, the solution was still quickly stirred for 20 h. Then the solution was stirred in an oil bath at 80° C. reflux for 4 h to obtain intermediate product hexahydropyrimidine as a colorless, fuming, and viscous liquid. $K_2CO_3$, KI, and anhydrous acetonitrile were added, followed by quick stirring to form a solid-liquid mixture. Then β-chloropropionitrile was added at 60° C. within 0.5 h. The mixture was stirred for 17 h, and cooled to room temperature. Then the mixture was subjected to separation and purification to obtain A1. Carbon nuclear magnetic resonance spectroscopy was shown in FIG. 1.

Synthesis of the Additive A2:

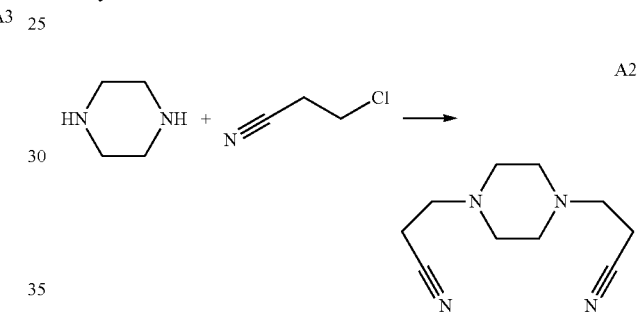

Anhydrous sodium carbonate, piperazine, and β-chloropionitrile were mixed in absolute ethanol, and stirred for 4 h for reaction. The mixture was repeatedly washed with hot ethanol for a plurality of times to obtain a crude product, and subjected to recrystallization to obtain A2. Carbon nuclear magnetic resonance spectroscopy was shown in FIG. 2.

Synthesis of the Additive A3:

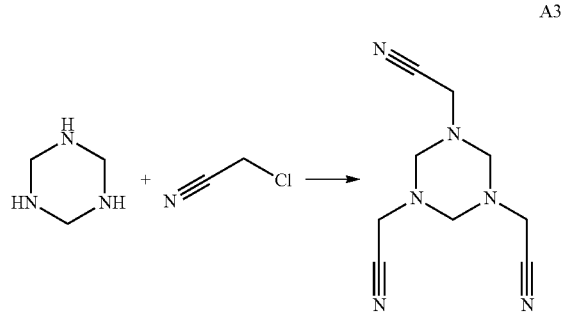

Anhydrous sodium carbonate, 1,3,5-s-triazine, and chloroacetonitrile were mixed in absolute ethanol, and stirred for 4 h for reaction. The mixture was repeatedly washed with hot ethanol for a plurality of times to obtain a crude product, and subjected to recrystallization to obtain A3. Carbon nuclear magnetic resonance spectroscopy was shown in FIG. 3.

In Examples 1-30 and Comparative Examples 1-2, lithium-ion batteries was prepared according to the following method.

(1) Preparation of an Electrolyte

A mixed solution of ethylene carbonate (EC for short), ethyl methyl carbonate (EMC for short) and diethyl carbonate (DEC for short) was used as an organic solvent, where a mass ratio of EC, EMC, and DEC was 1:1:1. $LiPF_6$ was used as a lithium salt in an amount of 12.5% relative to the total mass of the electrolyte. Additives were added according to electrolyte composition as shown in Table 1, where percents of all additive components are calculated relative to the total mass of the electrolyte.

Additives A used in the Examples and Comparative Examples were abbreviated as follows:

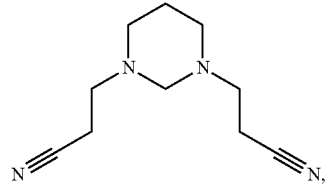
A1

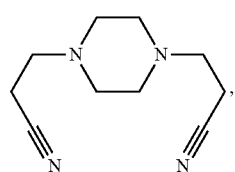
A2

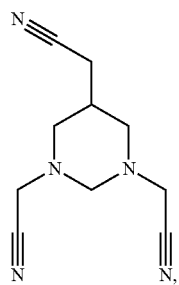
A3

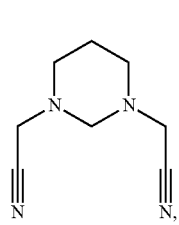
A4

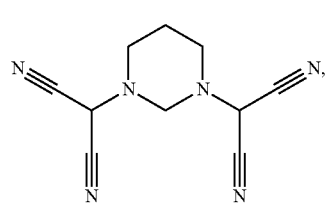
A5

-continued

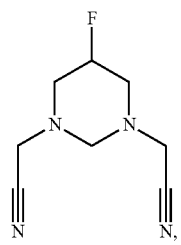
A6

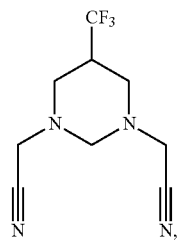
A7

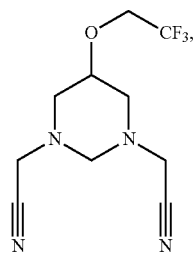
A8

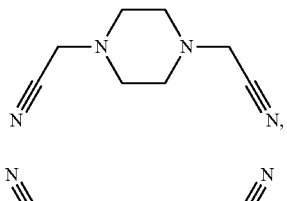
A9

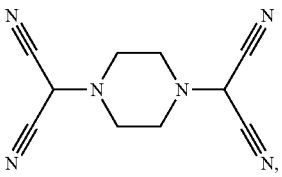
A10

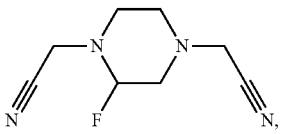
A11

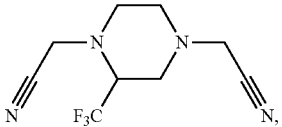
A12

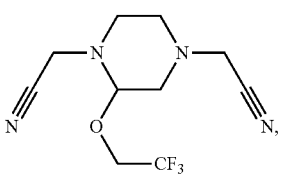
A13

-continued

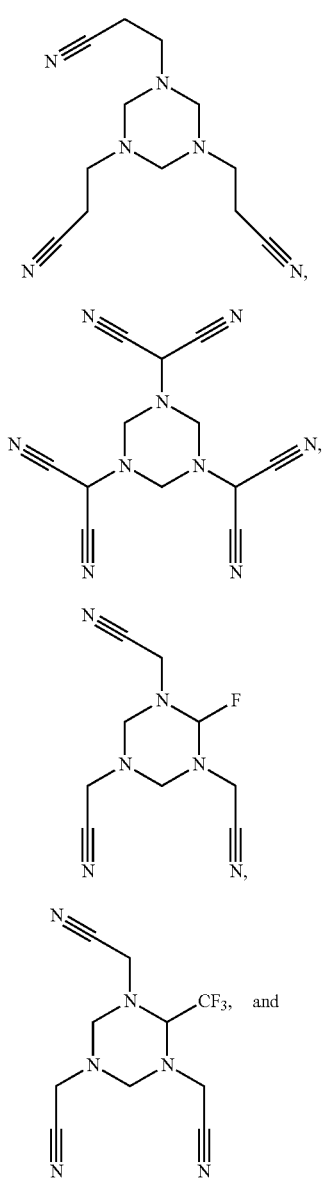

A14

A15

A16

A17

-continued

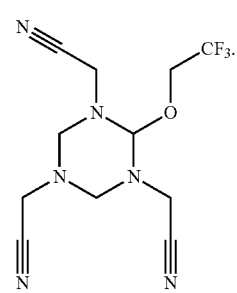

A18

(2) Preparation of a Positive Electrode Plate

A positive active material, a binder PVDF, and a conductive agent acetylene black in Table 2 based on a mass ratio of 98:1:1 were mixed. N-methylpyrrolidone was added. The resulting mixture was stirred by using a vacuum mixer until the mixture was stable and uniform, to obtain a positive slurry. The positive slurry was uniformly applied onto an aluminum foil. The aluminum foil was dried at room temperature, and transferred to a blast oven at 120° C. for 1 h. Then the aluminum foil was cold-pressed and cut to obtain a positive electrode plate.

(3) Preparation of a Negative Electrode Plate

A negative active material, a conductive agent acetylene black, a thickening agent sodium carboxymethyl cellulose, and a binder styrene-butadiene rubber in Table 2 based on a mass ratio of 97:1:1:1 were mixed. Deionized water was add. The resulting mixture was stirred by using a vacuum mixer until the mixture was stable and uniform, to obtain a negative slurry. The negative slurry was uniformly applied onto a copper foil. The copper foil was dried at room temperature, and transferred to a blast oven at 120° C. for 1 h. Then the copper foil was cold-pressed and cut to obtain a negative electrode plate.

(4) Preparation of a Lithium-Ion Battery

The positive electrode plate, the negative electrode plate, and a PP/PE/PP separator were wound to obtain an electrode assembly. The electrode assembly was placed into an aluminum-plastic film of a packaging bag, followed by injection of the electrolyte. Then a procedure including sealing, standing, hot and cold pressing, forming, gas exhausting, and capacity testing were performed to obtain a lithium-ion battery.

TABLE 1

Parameters of electrolyte in Examples 1-30 and Comparative Examples 1-2

|  | Additive A | | Additive B | | Additive C | |
| --- | --- | --- | --- | --- | --- | --- |
|  | Type | Amount | Type | Amount | Type | Amount |
| Example 1 | A1 | 0.1% | Acetic anhydride | 2.0% | FEC | 8.0% |
| Example 2 | A1 | 1.0% | Acetic anhydride | 2.0% | FEC | 8.0% |
| Example 3 | A1 | 2.0% | Acetic anhydride | 2.0% | FEC | 8.0% |
| Example 4 | A1 | 4.0% | Acetic anhydride | 2.0% | FEC | 8.0% |
| Example 5 | A1 | 6.0% | Acetic anhydride | 2.0% | FEC | 8.0% |
| Example 6 | A1 | 8.0% | Acetic anhydride | 2.0% | FEC | 8.0% |
| Example 7 | A1 | 10.0% | Acetic anhydride | 2.0% | FEC | 8.0% |
| Example 8 | A2 | 2.0% | Succinic anhydride | 0.1% | DFEC | 8.0% |
| Example 9 | A2 | 2.0% | Succinic anhydride | 1.0% | DFEC | 8.0% |
| Example 10 | A2 | 2.0% | Succinic anhydride | 2.0% | DFEC | 8.0% |
| Example 11 | A2 | 2.0% | Succinic anhydride | 3.0% | DFEC | 8.0% |
| Example 12 | A2 | 2.0% | Succinic anhydride | 5.0% | DFEC | 8.0% |
| Example 13 | A2 | 2.0% | Succinic anhydride | 7.0% | DFEC | 8.0% |
| Example 14 | A2 | 2.0% | Succinic anhydride | 10.0% | DFEC | 8.0% |
| Example 15 | A3 | 2.0% | Maleic anhydride | 2.0% | FEC | 0.1% |

TABLE 1-continued

Parameters of electrolyte in Examples 1-30 and Comparative Examples 1-2

|  | Additive A | | Additive B | | Additive C | |
| --- | --- | --- | --- | --- | --- | --- |
|  | Type | Amount | Type | Amount | Type | Amount |
| Example 16 | A3 | 2.0% | Maleic anhydride | 2.0% | FEC | 3.0% |
| Example 17 | A3 | 2.0% | Maleic anhydride | 2.0% | FEC | 5.0% |
| Example 18 | A3 | 2.0% | Maleic anhydride | 2.0% | FEC | 8.0% |
| Example 19 | A3 | 2.0% | Maleic anhydride | 2.0% | FEC | 15.0% |
| Example 20 | A3 | 2.0% | Maleic anhydride | 2.0% | FEC | 20.0% |
| Example 21 | A3 | 2.0% | Maleic anhydride | 2.0% | FEC | 30.0% |
| Example 22 | A1 | 2.0% | Propionic anhydride | 2.0% | FEC | 8.0% |
| Example 23 | A2 | 2.0% | Butyric anhydride | 2.0% | FEC | 8.0% |
| Example 24 | A3 | 2.0% | Valeric anhydride | 2.0% | FEC | 8.0% |
| Example 25 | A1 | 2.0% | Phthalic anhydride | 2.0% | FEC | 8.0% |
| Example 26 | A2 | 2.0% | Phthalic anhydride | 2.0% | FEC | 8.0% |
| Example 27 | A3 | 2.0% | Phthalic anhydride | 2.0% | FEC | 8.0% |
| Example 28 | A1 | 2.0% | Glutaric anhydride | 2.0% | FEC | 8.0% |
| Example 29 | A2 | 2.0% | Glutaric anhydride | 2.0% | FEC | 8.0% |
| Example 30 | A3 | 2.0% | Glutaric anhydride | 2.0% | FEC | 8.0% |
| Comparative Example 1 | / | / | / | / | / | / |
| Comparative Example 2 | Adiponitrile | 2.0% | / | / | / | / |

|  | Positive active material | Negative active material |
| --- | --- | --- |
| Example 1 | $Li_{1.01}Co_{0.98}Mg_{0.01}Ti_{0.005}Al_{0.005}O_2$ | Artificial graphite + Si |
| Example 2 | $Li_{1.01}Co_{0.98}Mg_{0.01}Ti_{0.005}Al_{0.005}O_2$ | Artificial graphite + $SiO_{x2}$ |
| Example 3 | $Li_{1.01}Co_{0.98}Mg_{0.01}Ti_{0.005}Al_{0.005}O_2$ | Natural graphite + Si |
| Example 4 | $Li_{1.01}Co_{0.98}Mg_{0.01}Ti_{0.005}Al_{0.005}O_2$ | Natural graphite + $SiO_{x2}$ |
| Example 5 | $Li_{1.01}Co_{0.98}Mg_{0.01}Ti_{0.005}Al_{0.005}O_2$ | Hard carbon |
| Example 6 | $Li_{1.01}Co_{0.98}Mg_{0.01}Ti_{0.005}Al_{0.005}O_2$ | Soft carbon |
| Example 7 | $Li_{1.01}Co_{0.98}Mg_{0.01}Ti_{0.005}Al_{0.005}O_2$ | Hard carbon + Si |
| Example 8 | $Li_{0.07}Co_{0.97}Zr_{0.01}Ti_{0.01}Al_{0.01}O_{1.9}S_{0.1}$ | Hard carbon + $SiO_{x2}$ |
| Example 9 | $Li_{0.07}Co_{0.97}Zr_{0.01}Ti_{0.01}Al_{0.01}O_{1.9}S_{0.1}$ | Soft carbon + Si |
| Example 10 | $Li_{0.07}Co_{0.97}Zr_{0.01}Ti_{0.01}Al_{0.01}O_{1.9}S_{0.1}$ | Soft carbon + $SiO_{x2}$ |
| Example 11 | $Li_{0.07}Co_{0.97}Zr_{0.01}Ti_{0.01}Al_{0.01}O_{1.9}S_{0.1}$ | Artificial graphite + Si |
| Example 12 | $Li_{0.07}Co_{0.97}Zr_{0.01}Ti_{0.01}Al_{0.01}O_{1.9}S_{0.1}$ | Artificial graphite + $SiO_{x2}$ |
| Example 13 | $Li_{0.07}Co_{0.97}Zr_{0.01}Ti_{0.01}Al_{0.01}O_{1.9}S_{0.1}$ | Natural graphite + Si |
| Example 14 | $Li_{0.07}Co_{0.97}Zr_{0.01}Ti_{0.01}Al_{0.01}O_{1.9}S_{0.1}$ | Natural graphite + $SiO_{x2}$ |
| Example 15 | $Li_{1.05}Co_{0.97}Mg_{0.01}Zr_{0.01}Al_{0.01}O_{1.9}Cl_{0.1}$ | Hard carbon |
| Example 16 | $Li_{1.05}Co_{0.97}Mg_{0.01}Zr_{0.01}Al_{0.01}O_{1.9}Cl_{0.1}$ | Soft carbon |
| Example 17 | $Li_{1.05}Co_{0.97}Mg_{0.01}Zr_{0.01}Al_{0.01}O_{1.9}Cl_{0.1}$ | Hard carbon + Si |
| Example 18 | $Li_{1.05}Co_{0.97}Mg_{0.01}Zr_{0.01}Al_{0.01}O_{1.9}Cl_{0.1}$ | Hard carbon + $SiO_{x2}$ |
| Example 19 | $Li_{1.05}Co_{0.97}Mg_{0.01}Zr_{0.01}Al_{0.01}O_{1.9}Cl_{0.1}$ | Soft carbon + Si |
| Example 20 | $Li_{1.05}Co_{0.97}Mg_{0.01}Zr_{0.01}Al_{0.01}O_{1.9}Cl_{0.1}$ | Soft carbon + $SiO_{x2}$ |
| Example 21 | $Li_{1.05}Co_{0.97}Mg_{0.01}Zr_{0.01}Al_{0.01}O_{1.9}Cl_{0.1}$ | Artificial graphite + Si |
| Example 22 | $Li_{1.05}Co_{0.98}Mg_{0.005}Zr_{0.005}Ti_{0.01}O_{1.9}F_{0.1}$ | Artificial graphite + $SiO_{x2}$ |
| Example 23 | $Li_{1.1}Co_{0.95}Mg_{0.01}Zr_{0.01}Al_{0.03}O_2$ | Natural graphite + Si |
| Example 24 | $Li_{1.04}Co_{0.95}Mg_{0.02}Zr_{0.03}O_{1.95}F_{0.05}$ | Natural graphite + $SiO_{x2}$ |
| Example 25 | $Li_{1.06}Co_{0.96}Mg_{0.02}Ti_{0.02}O_2$ | Hard carbon |
| Example 26 | $Li_{1.08}Co_{0.97}Mg_{0.01}Zr_{0.01}Al_{0.01}O_{1.9}S_{0.1}$ | Soft carbon |
| Example 27 | $Li_{1.09}Co_{0.98}Mg_{0.01}Ti_{0.005}Al_{0.005}O_2$ | Hard carbon + Si |
| Example 28 | $Li_{1.085}Co_{0.98}Zr_{0.01}Ti_{0.005}Al_{0.005}O_{1.9}Cl_{0.1}$ | Hard carbon + $SiO_{x2}$ |
| Example 29 | $Li_{1.03}Co_{0.96}Mg_{0.01}Zr_{0.01}Ti_{0.01}Al_{0.01}O_2$ | Soft carbon + Si |
| Example 30 | $Li_{1.04}Co_{0.97}Zr_{0.01}Al_{0.02}O_{1.9}F_{0.1}$ | Soft carbon + $SiO_{x2}$ |
| Comparative Example 1 | $LiCoO_2$ | Artificial graphite + Si |
| Comparative Example 2 | $Li_{1.04}Co_{0.97}Zr_{0.01}Al_{0.02}O_{1.9}F0.1$ | Artificial graphite + $SiO_{x2}$ |

Tests for lithium-ion battery are described below.

(1) Cycle Performance Test for a Lithium-Ion Battery at Normal Temperature and High Voltage At 25° C., the lithium-ion battery is charged at a constant current of 1 C until a voltage of 4.35 V is reached, further charged at a constant voltage of 4.35 V until a current of 0.05 C is reached, and then discharged at a constant current of 1 C until a voltage of 3.0 V is reached. This is a charge/discharge cycle process, and the obtained discharge capacity at this time is the discharge capacity at the first cycle. A lithium-ion battery is subjected to charge/discharge test according to the foregoing method for 200 cycles, to determine discharge capacity at the $200^{th}$ cycle.

Capacity retention rate (%) of a lithium-ion battery after 200 cycles=(the discharge capacity of the lithium-ion battery after 200 cycles/the discharge capacity of the lithium-ion battery at the first cycle)×100%.

(2) Cycle Performance Test for a Lithium-Ion Battery Under High-Temperature and High-Voltage Conditions At 45° C., the lithium-ion battery is charged at a constant current of 1 C until a voltage of 4.35 V is reached, further charged at a constant voltage of 4.35 V until a current of 0.05

C is reached, and then discharged at a constant current of 1 C until a voltage of 3.0 V is reached. This is a charge/discharge cycle process, and the obtained discharge capacity at this time is the discharge capacity at the first cycle. A lithium-ion battery is subjected to charge/discharge test according to the foregoing method for 200 cycles, to determine a discharge capacity at the $200^{th}$ cycle.

Capacity retention rate (%) of a lithium-ion battery after 200 cycles=(the discharge capacity of the lithium-ion battery after 200 cycles/the discharge capacity of the lithium-ion battery at the first cycle)×100%.

(3) Storage Performance Test for a Lithium-Ion Battery at High Temperature

At 25° C., the lithium-ion battery is charged at a constant current of 0.5 C until a voltage of 4.35 V is reached, and then charged at a constant voltage of 4.35 V until a current of 0.05 C is reached. Thickness of the lithium-ion battery is tested and denoted as $h_0$. Then the lithium-ion battery is placed in a constant-temperature box at 85° C., stored for 24 h, and then taken out. Then the thickness of the lithium-ion battery is tested again and denoted as $h_1$.

Thickness expansion rate (%) of the lithium-ion battery after storage at 85° C. for 24 h=[($h_1$–$h_0$)/$h_0$]×100%.

The lithium-ion batteries were tested in the above tests.

|  | Capacity retention rate after 200 cycles at 25° C./4.35 V | Capacity retention rate after 200 cycles at 45° C./4.35 V | Thickness expansion rate at 85° C./24 h |
|---|---|---|---|
| Example 1 | 87% | 84% | 16% |
| Example 2 | 95% | 91% | 8% |
| Example 3 | 98% | 95% | 4% |
| Example 4 | 96% | 92% | 4% |
| Example 5 | 92% | 90% | 3% |
| Example 6 | 87% | 78% | 2% |
| Example 7 | 74% | 62% | 1% |
| Example 8 | 92% | 90% | 14% |
| Example 9 | 95% | 92% | 9% |
| Example 10 | 97% | 94% | 4% |
| Example 11 | 96% | 93% | 5% |
| Example 12 | 94% | 91% | 8% |
| Example 13 | 92% | 90% | 10% |
| Example 14 | 89% | 86% | 21% |
| Example 15 | 87% | 80% | 16% |
| Example 16 | 90% | 84% | 9% |
| Example 17 | 94% | 91% | 7% |
| Example 18 | 97% | 95% | 4% |
| Example 19 | 90% | 84% | 11% |
| Example 20 | 84% | 72% | 16% |
| Example 21 | 75% | 58% | 34% |
| Example 22 | 97% | 95% | 4% |
| Example 23 | 96% | 93% | 4% |
| Example 24 | 94% | 95% | 3% |
| Example 25 | 97% | 93% | 3% |
| Example 26 | 98% | 96% | 4% |
| Example 27 | 92% | 90% | 2% |
| Example 28 | 99% | 97% | 1% |
| Example 29 | 96% | 96% | 2% |
| Example 30 | 95% | 97% | 2% |
| Comparative Example 1 | 81% | 73% | 52% |
| Comparative Example 2 | 85% | 78% | 21% |

It can be seen from comparisons between Examples 1-30 and Comparative Examples 1-2 that the lithium-ion batteries of this application have super cycle performance and storage performance under high-temperature and high-voltage conditions.

Compared with Comparative Example 1, in Examples, the metal ion M-doped lithium cobalt oxide material $Li_{x1}Co_{y1}M_{1-y1}O_{2-z1}Q_{z1}$ was used as the positive active material, and a combination of additives including the additive A, the additive B, and the additive C was used as electrolyte additives. The doping element M served as a framework in the positive active material. This reduced lattice deformation of the positive active material during deep delithiation, delayed degradation of bulk structure of the positive active material, and greatly improved structural stability of the lithium-ion battery when the lithium-ion battery was used at high voltage. The additive A was a polynitrile six-membered nitrogen-heterocyclic compound with a relatively low oxidation potential, such that a stable complex layer was formed on a surface of the positive active material during formation of the battery. This effectively passivated the surface of the positive active material, reduced surface activity of the positive active material, and avoided direct contact between the electrolyte and the surface of the positive active material, thereby greatly reducing surface side reactions, and correspondingly reducing lithium ions consumed in the side reactions, and thus greatly decreasing a consumption rate of reversible lithium ions. The actual effect finally manifested was that capacity retention rate of the lithium-ion battery after cycling was greatly increased. Due to the production of gas in some surface side reactions, the reduction of surface side reactions further indicated a decrease in gas production of the battery. The actual effect finally manifested was that thickness expansion of the lithium-ion battery was obviously reduced at high temperature. The additive B absorbed moisture in the electrolyte, thereby preventing generation of HF in the electrolyte which may cause corrosion and damage to the surface of the positive active material. The additive B had certain acidity after absorbing moisture, so as to neutralize alkalinity on the surface of the positive active material, and reduce a decomposition effect of an alkaline metal oxide on an organic solvent such as carbonate in the positive active material. The additive C formed a uniform, thin, and resilient SEI film on a surface of a negative electrode to avoid electron conduction between the negative electrode and the electrolyte, thereby effectively reducing side reactions between the negative electrode and the electrolyte, and suppressing a continuous increase in negative electrode impedance. In addition, resilience of the protective film further suppressed swelling of the negative electrode, and prevented continuous consumption of the electrolyte due to excessive rupture of the SEI film. Thus, this application could significantly improve cycle performance and storage performance of the lithium-ion battery under high-temperature and high-voltage conditions.

Compared with the linear nitrile compound used in Comparative Example 2, the polynitrile six-membered nitrogen-heterocyclic compound in Examples had a special six-membered nitrogen-heterocyclic structure with a spacing between nitrile groups closer to that between transition metals on the surface of the positive active material. This could maximize complexation of the nitrile groups and allow more nitrile groups to have a complexation effect. Therefore, the polynitrile six-membered nitrogen-heterocyclic compound in Examples had stronger coverage on a transition metal on the surface of the positive active material, better passivation on the surface of the positive active material, and also outstanding improvement on cycle performance and storage performance of the lithium-ion battery.

It can be further seen from Examples 1-7 that, when an end-of-charge voltage was fixed at 4.35 V, with an increase (from 0.1% to 10%) in the amount of the additive A, the capacity retention rate of the lithium-ion battery after cycling at 25° C. and 45° C. showed an ascent and then showed a decline trend, and the thickness expansion rate after storage at 85° C. for 24 h was decreasing. This was because when the amount of the additive A was relatively large, the complex layer formed by the additive A being adsorbed on the surface of the positive active material was likely to be thicker and denser, affecting diffusion and migration of lithium ions, and greatly increasing positive electrode impedance. Secondly, the additive A consumed lithium ions while forming the complex layer, reducing lithium ions available for cycling. Finally, a relatively large amount of the additive A caused an increase in overall viscosity of the electrolyte and a decrease in an ionic conductivity, so that the capacity retention rate of the lithium-ion battery after cycling at 25° C. and 45° C. showed an ascent and then showed a decline trend. Therefore, the amount of the additive A needs to be appropriate. Preferably, the amount is 0.1%-10%; more preferably, is 0.1%-6%; furthermore preferably, is 0.1%-3.5%.

It can be learned from Examples 8-14 that, when an end-of-charge voltage is fixed at 4.35 V, with an increase (from 0.1% to 10%) in an amount of the additive B, the capacity retention rate of the lithium-ion battery after cycling at 25° C. and 45° C. showed an ascent and then showed a decline trend, and the thickness expansion rate after storage at 85° C. for 24 h decreased and then showed an increase trend. This was because when the amount of the additive B was relatively large, an acidity of a product produced by the additive B absorbing moisture increased, thereby imposing some corrosive effect on the positive active material, and further affecting cycle performance and storage performance of the lithium-ion battery. Therefore, the amount of the additive B needs to be appropriate. Preferably, the amount is 0.1%-10%; more preferably, is 0.1%-5%.

It can be further seen from Examples 15-21 that, when an end-of-charge voltage was fixed at 4.35 V, with an increase (from 0.1% to 30%) in an amount of the additive C, the capacity retention rate of the lithium-ion battery after cycling at 25° C. and 45° C. showed an ascent and then showed a decline trend, and the thickness expansion rate after storage at 85° C. for 24 h decreased and then showed an increase trend. This was because when the amount of the additive C was relatively large, a relatively thick film was likely to be formed at the negative electrode, increasing negative electrode impedance. In addition, due to relatively poor thermal stability and easy decomposition of the additive C, when the amount of the additive C was relatively large, the lithium-ion battery produced a large amount of gas, thereby resulting in bubbles and a fracturing bridge phenomenon of the electrolyte inside the battery and thus further increasing battery impedance, affecting cycle performance and storage performance of the lithium-ion battery. Therefore, the amount of the additive C needs to be appropriate. Preferably, the amount is 0.1%-30%; more preferably, is 5%-15%.

According to the disclosure and guidance in this specification, a person skilled in the art to which this application relates may also make appropriate changes and modifications to the foregoing embodiments. Therefore, this application is not limited to the specific embodiments disclosed and described above, and modifications and changes to this application shall also fall within the protection scope of the claims of this application. In addition, although some specific terms are used in this specification, these terms are merely intended for ease of description, and do not constitute any limitation on this application.

What is claimed is:

1. A lithium-ion battery, comprising an electrode assembly and an electrolyte, wherein the electrode assembly comprises a positive electrode plate, a negative electrode plate, and a separator,
   wherein
   a positive active material of the positive electrode plate comprises $Li_{x1}Co_{y1}M_{1-y1}O_{2-z1}Q_{z1}$, wherein $0.5 \leq x1 \leq 1.2$, $0.8 \leq y1 < 1.0$, $0 \leq z1 \leq 0.1$, M is selected from one or more of Al, Ti, Zr, Y, and Mg, and Q is selected from one or more of F, Cl, and S;
   the electrolyte contains an additive A, an additive B, and an additive C, wherein the additive A is selected from one or more of compounds represented by Formula I-1, Formula I-2, and Formula I-3, the additive B is selected from one or more of compounds represented by Formula II-1 and Formula II-2, and the additive C is selected from one or more of compounds represented by Formula III-1;

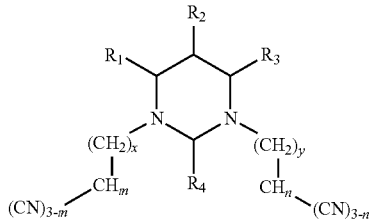

Formula I-1

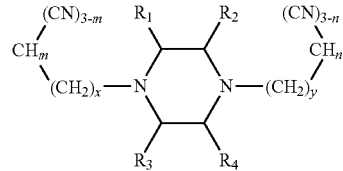

Formula I-2

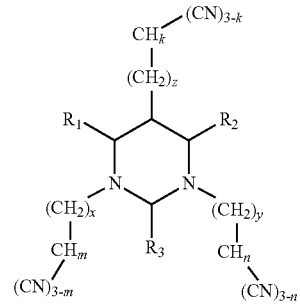

Formula I-3

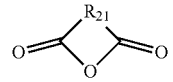

Formula II-1

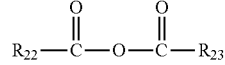

Formula II-2

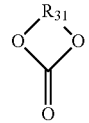

Formula III-1 in the Formula I-1, the Formula I-2, and the Formula I-3, $R_1$, $R_2$, $R_3$, and $R_4$ each are independently selected from a hydrogen atom, a halogen atom, a substituted or unsubstituted $C_1$-$C_{12}$ alkyl group, a substituted or unsubstituted $C_1$-$C_{12}$ alkoxy group, a substituted or unsubstituted $C_1$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, or a substituted or unsubstituted $C_2$-$C_{12}$ heterocyclic group, wherein a substituent group is selected from one or more of a halogen atom, a nitrile group, a $C_1$-$C_6$ alkyl group, a $C_2$-$C_6$ alkenyl group, and a $C_1$-$C_6$ alkoxy group; x, y, and z each are independently selected from integers 0-8; and m, n, and k each are independently selected from integers 0-2;

in the Formula II-1, $R_{21}$ is selected from a substituted or unsubstituted $C_2$-$C_{12}$ alkyl group, a substituted or unsubstituted $C_2$-$C_{12}$ alkoxy group, a substituted or unsubstituted $C_2$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, or a substituted or unsubstituted $C_2$-$C_{12}$ heterocyclic group, wherein a substituent group is selected from one or more of a halogen atom, a nitrile group, a $C_1$-$C_6$ alkyl group, a $C_2$-$C_6$ alkenyl group, and a $C_1$-$C_6$ alkoxy group;

in the Formula II-2, $R_{22}$ and $R_{23}$ each are independently selected from a hydrogen atom, a substituted or unsubstituted $C_1$-$C_{12}$ alkyl group, a substituted or unsubstituted $C_1$-$C_{12}$ alkoxy group, a substituted or unsubstituted $C_1$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, or a substituted or unsubstituted $C_2$-$C_{12}$ heterocyclic group, wherein a substituent group is selected from one or more of a halogen atom, a nitrile group, a $C_1$-$C_6$ alkyl group, a $C_2$-$C_6$ alkenyl group, and a $C_1$-$C_6$ alkoxy group;

in the Formula III-1, $R_{31}$ is selected from a halogen substituted $C_1$-$C_6$ alkylene group or a halogen substituted $C_2$-$C_6$ alkenylene group.

2. The lithium-ion battery according to claim 1, wherein in the Formula I-1, the Formula I-2, and the Formula I-3, $R_1$, $R_2$, $R_3$, and $R_4$ each are independently selected from a hydrogen atom, a halogen atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxy group, a substituted or unsubstituted $C_1$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group, wherein a substituent group is selected from halogen atoms;

x, y, and z each are independently selected from 0, 1, or 2;

m, n, and k each are independently selected from 1 or 2;

$R_{21}$ is selected from a substituted or unsubstituted $C_2$-$C_3$ linear or branched alkyl group, a substituted or unsubstituted $C_5$-$C_7$ cyclic alkyl group, a substituted or unsubstituted $C_2$-$C_3$ alkoxy group, a substituted or unsubstituted $C_2$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group, wherein a substituent group is selected from one or more of halogen atoms;

$R_{22}$ and $R_{23}$ each are independently selected from a substituted or unsubstituted $C_2$-$C_3$ linear or branched alkyl group, a substituted or unsubstituted $C_5$-$C_7$ cyclic alkyl group, a substituted or unsubstituted $C_2$-$C_3$ alkoxy group, a substituted or unsubstituted $C_2$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group, wherein a substituent group is selected from one or more of halogen atoms; and $R_{31}$ is selected from a halogen substituted $C_2$-$C_4$ alkylene group or a halogen substituted $C_2$-$C_4$ alkenylene group.

3. The lithium-ion battery according to claim 1, wherein in the Formula I-1, $R_1$ and $R_3$ are both hydrogen atoms;

in the Formula I-2, at least two of $R_1$, $R_2$, $R_3$, and $R_4$ are hydrogen atoms; and in the Formula I-3, at least two of $R_1$, $R_2$, and $R_3$ are hydrogen atoms.

4. The lithium-ion battery according to claim 1, wherein the additive A is selected from one or more of the following compounds:

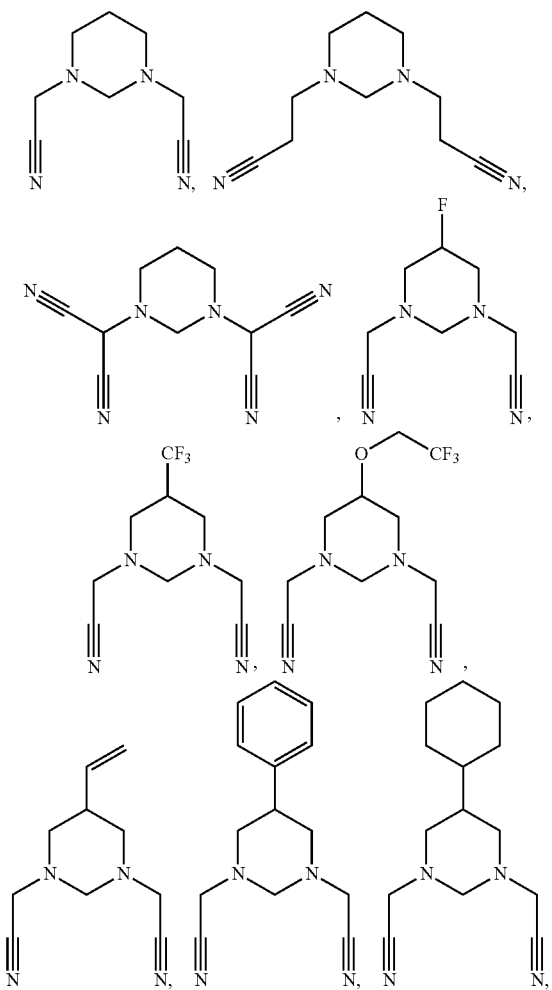

-continued

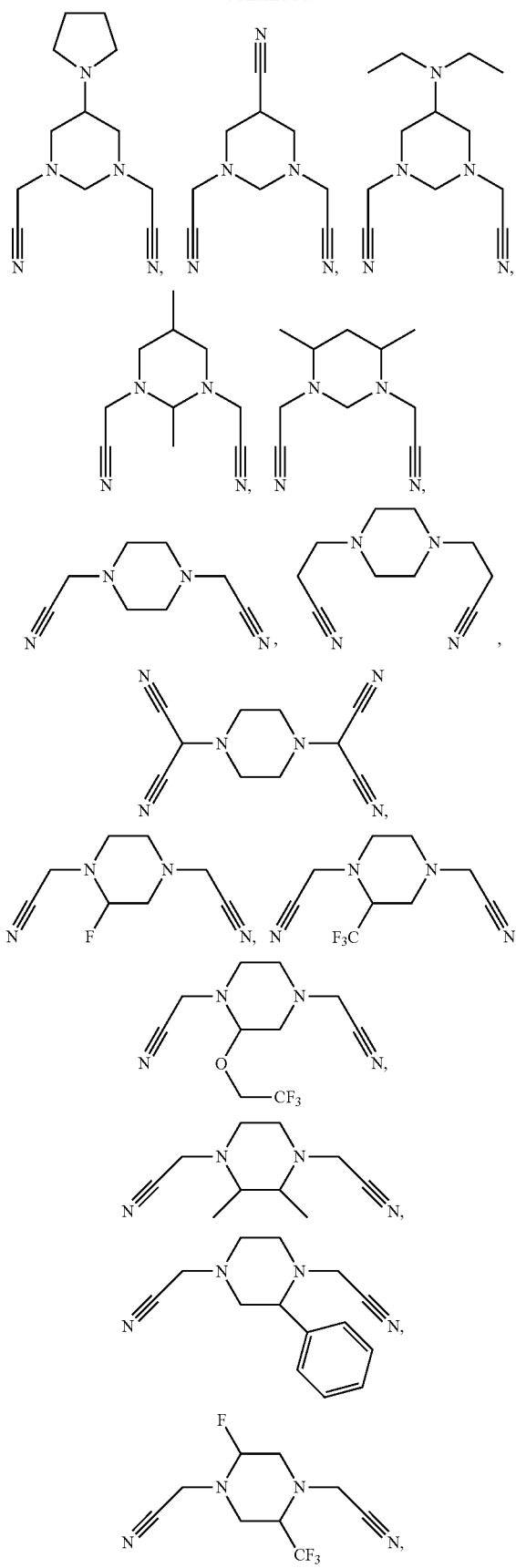

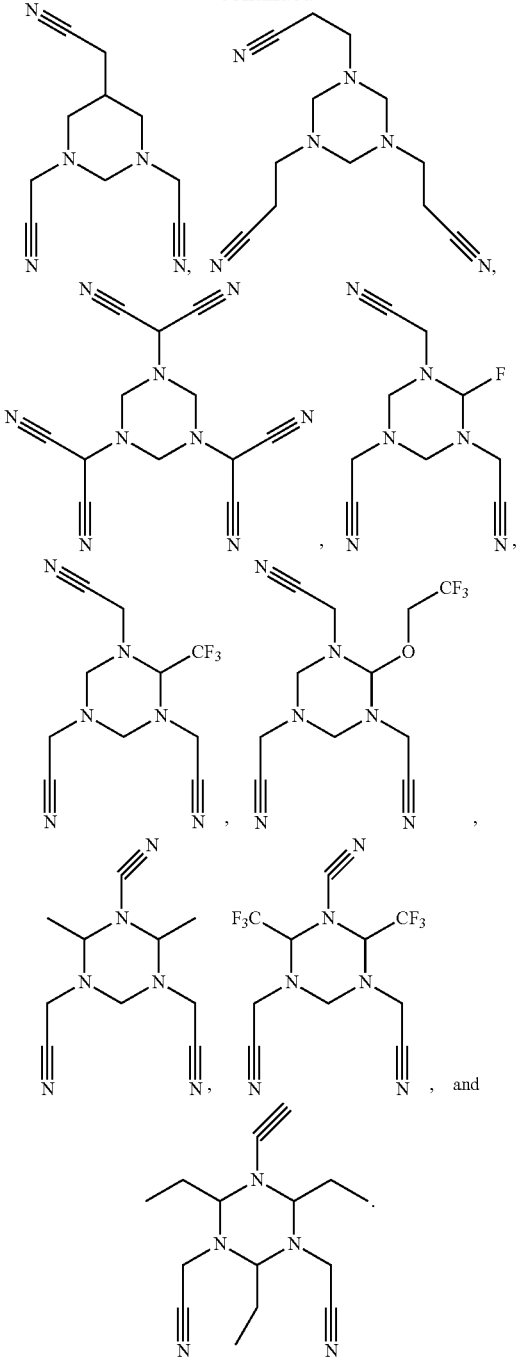

5. The lithium-ion battery according to claim 1, wherein the additive B is selected from one or more of succinic anhydride, glutaric anhydride, maleic anhydride, phthalic anhydride, acetic anhydride, propionic anhydride, butyric anhydride, and valeric anhydride.

6. The lithium-ion battery according to claim 1, wherein the additive C is selected from one or more of fluoroethylene carbonate, fluoropropylene carbonate, trifluoropropylene carbonate, and trans- or cis-4,5-difluoro-1,3-dioxolane-2-ketone.

7. The lithium-ion battery according to claim 1, wherein mass percent of the additive A in the electrolyte is 0.1%-10%;

mass percent of the additive B in the electrolyte is 0.1%-10%; and mass percent of the additive C in the electrolyte is 0.1%-30%.

8. The lithium-ion battery according to claim 1, wherein a conductivity of the electrolyte is 4 mS/cm-12 mS/cm.

9. The lithium-ion battery according to claim 1, wherein a negative active material of the negative electrode plate comprises one or more of Si, $SiO_{x2}$, Si/C composite material, and Si alloy, and $0<x2\leq2$.

10. The lithium-ion battery according to claim 1, wherein an end-of-charge voltage of the lithium-ion battery is not less than 4.2 V.

11. An apparatus, comprising the lithium-ion battery according to claim 1.

12. The lithium-ion battery according to claim 3, wherein $R_1$, $R_3$, and $R_4$ are all hydrogen atoms.

13. The lithium-ion battery according to claim 3, wherein at least three of $R_1$, $R_2$, $R_3$, and Ra are hydrogen atoms.

14. The lithium-ion battery according to claim 7, wherein mass percent of the additive A in the electrolyte is 0.1%-6%.

15. The lithium-ion battery according to claim 7, wherein mass percent of the additive A in the electrolyte is 0.1%-3.5%.

16. The lithium-ion battery according to claim 7, wherein mass percent of the additive B in the electrolyte is 0.1%-5%.

17. The lithium-ion battery according to claim 7, wherein mass percent of the additive C in the electrolyte is 5%-15%.

18. The lithium-ion battery according to claim 10, wherein an end-of-charge voltage of the lithium-ion battery is not less than 4.35 V.

* * * * *